United States Patent
Seeley et al.

(10) Patent No.: US 10,413,718 B2
(45) Date of Patent: *Sep. 17, 2019

(54) MODULAR LEAD END

(71) Applicant: Medtronic, Inc., Minneapolis, MN (US)

(72) Inventors: Dale F. Seeley, Spring Park, MN (US); Michael T. Hegland, Mounds View, MN (US)

(73) Assignee: Medtronic, Inc., Minneapolis, MN (US)

( * ) Notice: Subject to any disclaimer, the term of this patent is extended or adjusted under 35 U.S.C. 154(b) by 17 days.

This patent is subject to a terminal disclaimer.

(21) Appl. No.: 15/961,495

(22) Filed: Apr. 24, 2018

(65) Prior Publication Data

US 2018/0236219 A1    Aug. 23, 2018

Related U.S. Application Data

(63) Continuation of application No. 15/612,121, filed on Jun. 2, 2017, now Pat. No. 9,962,539, which is a (Continued)

(51) Int. Cl.
*A61B 5/00* (2006.01)
*A61B 5/042* (2006.01)
*A61N 1/05* (2006.01)

(52) U.S. Cl.
CPC .............. *A61N 1/05* (2013.01); *A61B 5/6867* (2013.01); *A61B 5/042* (2013.01); (Continued)

(58) Field of Classification Search
CPC ................ A61N 1/05; Y10T 29/49208; Y10T 29/49174; H01R 2201/12; H01R 13/5224; (Continued)

(56) References Cited

U.S. PATENT DOCUMENTS 5,458,629 A    10/1995 Baudino et al.
5,855,552 A    1/1999 Houser et al.
(Continued)

FOREIGN PATENT DOCUMENTS

WO    WO 2008/060142    5/2008
WO    WO 2013/062863    5/2013

OTHER PUBLICATIONS

PCT/US2012/060935—International Search Report and Written Opinion, dated Jan. 23, 2013.
(Continued)

*Primary Examiner* — Truc T Nguyen
*Assistant Examiner* — Milagros Jeancharles
(74) *Attorney, Agent, or Firm* — Mueting, Raasch & Gebhardt, P.A.

(57) ABSTRACT

Various embodiments of this disclosure concern assembly of a lead having one or two modular lead ends. A modular lead end can be made by aligning a plurality of wires exposed on an end of a main lead body with a plurality of conductors exposed on an end of a lead end. The lead end may comprise a spine, the plurality of conductors circumferentially arrayed about the spine, and an outer surface comprising a plurality of exposed electrical elements and polymer material, the plurality of electrical elements arrayed on the spine and electrically connected with the plurality of conductors. The assembly can further include making electrical connections between the plurality of electrical wires and the plurality of conductors and insulating the plurality of wires and the plurality of conductors.

12 Claims, 16 Drawing Sheets

Related U.S. Application Data continuation of application No. 15/226,207, filed on Aug. 2, 2016, now Pat. No. 9,713,705, which is a continuation of application No. 14/354,422, filed as application No. PCT/US2012/060935 on Oct. 19, 2012, now Pat. No. 9,421,362.

(60) Provisional application No. 61/552,891, filed on Oct. 28, 2011.

(52) U.S. Cl.
CPC ... *A61B 2562/0209* (2013.01); *A61B 2562/12* (2013.01); *A61B 2562/222* (2013.01); *A61B 2562/227* (2013.01); *Y10T 29/49174* (2015.01); *Y10T 29/49208* (2015.01)

(58) Field of Classification Search
CPC .................. A61B 5/6867; A61B 5/042; A61B 2526/0209; A61B 2526/12; A61B 2526/222; A61B 2526/227
USPC ................. 439/607, 609, 669, 701, 724, 71, 439/907–909, 715, 594, 928
See application file for complete search history.

(56) References Cited

U.S. PATENT DOCUMENTS

| | | |
|---|---|---|
| 5,935,159 A | 8/1999 | Cross, Jr. et al. |
| 7,108,549 B2 | 9/2006 | Lyu et al. |
| 7,130,700 B2 | 10/2006 | Gardeski |
| 7,184,838 B2 | 2/2007 | Cross, Jr. |
| 7,326,083 B2 | 2/2008 | Mehdizadeh et al. |
| 7,437,197 B2 | 10/2008 | Harris et al. |
| 7,499,755 B2 | 3/2009 | Cross, Jr. |
| 7,680,544 B1 | 3/2010 | Conger |
| 7,890,175 B1 | 2/2011 | Rey et al. |
| 7,912,557 B1 | 3/2011 | Randle et al. |
| 8,204,570 B2 | 6/2012 | Sinderby et al. |
| 8,326,434 B2 | 12/2012 | Skubitz et al. |
| 8,406,896 B2 | 3/2013 | McDonald et al. |
| 8,567,055 B2 | 10/2013 | Fan et al. |
| 8,634,936 B2 | 1/2014 | Klardie et al. |
| 8,706,229 B2 | 4/2014 | Lahti et al. |
| 8,911,265 B2 | 12/2014 | Di Maio et al. |
| 9,101,776 B2 | 8/2015 | Hughes |
| 9,421,362 B2 | 8/2016 | Seeley et al. |
| 9,713,705 B2 | 7/2017 | Seeley et al. |
| 9,962,539 B2 * | 5/2018 | Seeley ............. A61N 1/05 |
| 2004/0097965 A1 | 5/2004 | Gardeski et al. |
| 2005/0182470 A1 | 8/2005 | Cross, Jr. |
| 2005/0234522 A1 | 10/2005 | Ley et al. |
| 2007/0168004 A1 | 7/2007 | Walter |
| 2008/0188919 A1 | 8/2008 | Bartels et al. |
| 2009/0012591 A1 | 1/2009 | Barker |
| 2009/0143846 A1 | 6/2009 | Cross, Jr. |
| 2009/0222073 A1 | 9/2009 | Flowers et al. |
| 2009/0234407 A1 | 9/2009 | Hastings et al. |
| 2010/0305670 A1 | 12/2010 | Hall et al. |
| 2011/0022100 A1 | 1/2011 | Brase et al. |
| 2011/0072659 A1 | 3/2011 | Swanson et al. |
| 2011/0106189 A1 | 5/2011 | Seeley et al. |
| 2011/0165785 A1 | 7/2011 | Lindner et al. |
| 2011/0220408 A1 | 9/2011 | Walsh et al. |
| 2011/0245887 A1 | 10/2011 | Klardie et al. |
| 2012/0041295 A1 | 2/2012 | Schultz |
| 2015/0165217 A1 | 6/2015 | Hughes |

OTHER PUBLICATIONS

PCT/US2012/060988—International Search Report and Written Opinion, dated Jan. 31, 2013.

* cited by examiner

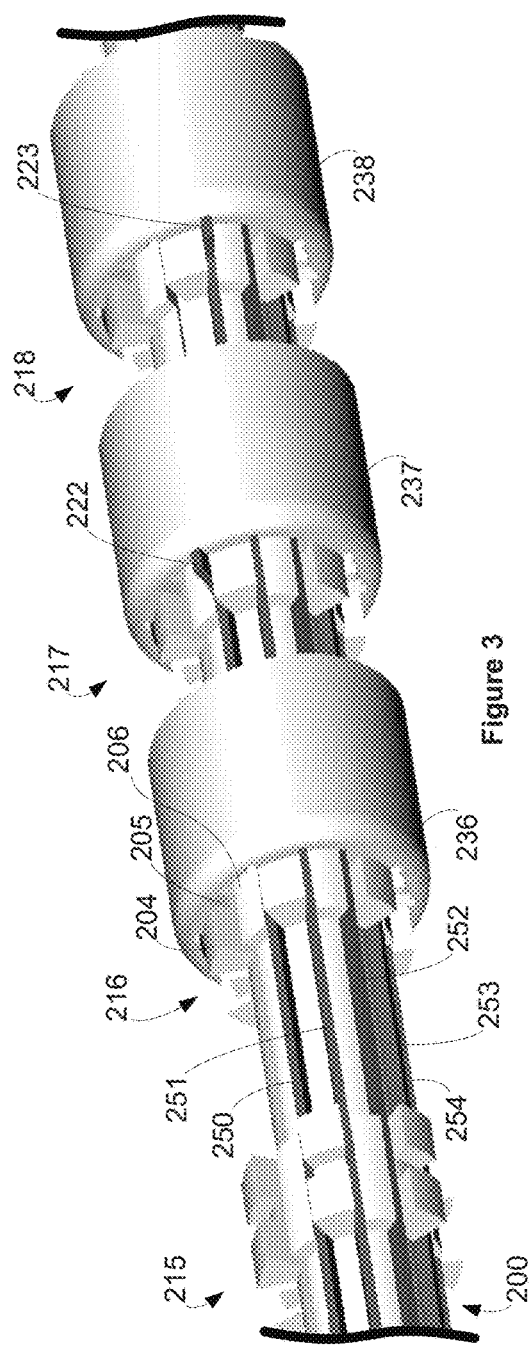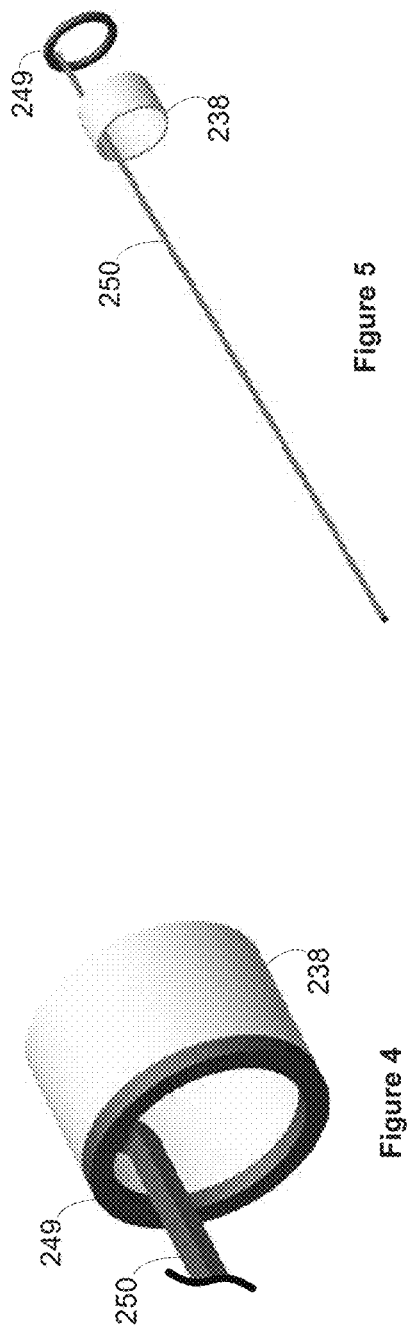

MODULAR LEAD END

This application is a continuation of U.S. patent application Ser. No. 15/612,121, filed Jun. 2, 2017, which is a continuation of U.S. patent application Ser. No. 15/226,207, filed Aug. 2, 2016, now issued as U.S. Pat. No. 9,713,705, which is a continuation of U.S. patent application Ser. No. 14/354,422, filed Apr. 25, 2014, now issued as U.S. Pat. No. 9,421,362, which is a U.S. national stage entry of International Application No. PCT/2012/060935, filed Oct. 19, 2012, which claims the benefit of U.S. Provisional Patent Application No. 61/552,891, filed Oct. 28, 2011, now expired. The entire contents of each of which are incorporated herein by reference.

TECHNICAL FIELD

The disclosure relates to medical leads, including implantable leads configured to conduct electrical energy between tissue and circuitry.

BACKGROUND OF THE INVENTION

Leads can be used to carry electrical energy between tissue and circuitry of a device, such as in sensing and/or stimulation applications. In the case of sensing, the electrical energy may be indicative of physiological activity while in a case of therapy delivery the electrical energy may comprise stimulation pulses. Leads may be partially or wholly implanted within a patient. For example, an implanted lead can carry electrical signals generated in a patient (e.g., by brain, heart, muscle tissue) to signal processing circuitry in an implanted housing for data collection and/or determination of a patient state. Additionally or alternatively, electrical stimulation can be delivered from stimulation circuitry within the housing to a targeted area of the patient (e.g., brain, heart, spine, one or more nerves, pelvic floor, muscles) through the lead. Typically, the lead and the housing are separate components that are connected to one another during an implantation procedure.

SUMMARY

In general, this disclosure concerns modular leads having a spine within one or both ends of the leads.

Various embodiments concern modular leads comprising a main lead body, the lead body comprising an elongated tube and a plurality of electrical wires, the plurality of electrical wires exposed on at least one end of the main lead body in an arrangement, and a lead end separate from the lead body, the lead end comprising an elongated spine having a length, an outer surface comprising a plurality of exposed electrical elements and an insulating material, the plurality of electrical elements positioned along the spine and configured for one or both of receiving electrical energy and delivering electrical energy, and a modular connector at one end of the lead end, the modular connector comprising a plurality of exposed conductors that are circumferentially arrayed about the spine, the plurality of conductors electrically connected with the plurality of electrical elements, wherein the arrangement of the plurality of electrical wires is complementary to the array of the conductors for making respective electrical connections between the plurality of electrical wires and the plurality of conductors.

In some modular lead embodiments, the spine has a plurality of paths along at least a portion of the length of the spine, wherein the plurality of conductors extend within the plurality of paths. In some cases, the paths are divided from each other by a plurality of projections, the plurality of projections extending outward along the spine. In some cases, the plurality of paths comprise a plurality of channels formed by the spine. In some further cases, the plurality of channels extend across a modular connector section of the spine and the conductors are at least partially within the plurality of channels.

In some modular leads, the plurality of electrical wires are splayed outward to form a circular pattern in the arrangement of the plurality of electrical wires. In some cases, the plurality of electrical wires of the arrangement are respectively aligned with the plurality of conductors. In some cases, the plurality of conductors are evenly spaced around the spine. In some embodiments, the plurality of electrical elements comprise rings that surround the spine.

In some cases, the plurality of electrical wires are supported in the arrangement by a hub. In some cases, the plurality of conductors are also supported in the array by the hub. In some embodiments, the hub comprises a plurality of holes, each electrical wire of the plurality extending into a different hole of the hub. In various embodiments, the hub comprises a plurality of metal sleeves, the metal sleeves being open on a first side of the hub and configured to receive each conductor of the plurality of conductors on the first side of the hub, the metal sleeves also being open on a second side of the hub and configured to receive each wire of the plurality of electrical wires on the second side of the hub. Each sleeve may have a window along the sleeve, the window large enough to permit welding within the sleeve through the window. In some embodiments, the hub comprises a plurality of channels, each electrical wire of the plurality extending within a respective channel of the plurality of channels. In some hub embodiments, the plurality of channels spiral around the hub.

Various embodiments concern a method of making a lead comprising aligning a plurality of electrical wires exposed on an end of a main lead body with a plurality of conductors exposed on an end of a lead end, the lead end comprising a spine, the plurality of conductors circumferentially arrayed about the spine, and an outer surface comprising a plurality of exposed electrical elements and polymer material, the plurality of electrical elements arrayed on the spine and electrically connected with the plurality of conductors. Such methods may further include making mechanical and electrical connections between the plurality of electrical wires and the plurality of conductors. Such methods may further include insulating the plurality of electrical wires and the plurality of conductors.

In various method embodiments, aligning the plurality of conductors comprising arranging the conductors exposed on the end of the main lead into a circular pattern. In some cases, the plurality of electrical wires in the circular pattern respectively align with the plurality of conductors circumferentially arrayed about the spine.

Various method embodiments may further comprise selecting the lead end from a plurality of lead end-types, each of the plurality of different lead end-types having a different exposed pattern of the plurality of electrical elements exposed on the exterior surface. In some cases, making mechanical and electrical connections between the plurality of electrical wires and the plurality of conductors comprises welding the plurality of electrical wires to the plurality of conductors.

In various method embodiments, aligning the plurality of electrical wires with the plurality of conductors is facilitated by a hub. Aligning of the plurality of electrical wires with the plurality of conductors may comprise inserting the plurality of electrical wires into a first plurality of holes on a first side of the hub and inserting the plurality of conductors into a plurality of second holes on the second side of the hub. In some cases, the first plurality of holes on the first side of the hub are respectively connected to the second plurality of holes on the second side of the hub by a plurality of metal sleeves. In some cases, making mechanical and electrical connections comprises welding the plurality of electrical wires and the plurality of conductors through windows in the plurality of metal sleeves. In some embodiments, the hub comprises a plurality of channels and aligning the plurality of electrical wires with the plurality of conductors comprising placing the plurality of electrical wires and the plurality of conductors into the channels. In some embodiments, the plurality of channels spiral around the hub.

Various method embodiments further comprising forming the lead end by spacing the plurality of exposed electrical elements along the spine, making electrical connections between the plurality of exposed electrical elements and the plurality of conductors, and forming the exterior surface by adding polymer between the plurality of exposed electrical elements.

In some method embodiments, insulating the plurality of electrical wires and the plurality of conductors comprises depositing polymer material around the mechanical connections between the plurality of electrical wires and the plurality of conductors to form a round lead exterior over the mechanical connections. In some method embodiments, the plurality of paths are evenly spaced from each other around the circumference of the spine.

Various method embodiments concern making a modular lead comprising selecting a lead end from a plurality of different lead ends, each lead end of the plurality comprising a spine, a plurality of conductors circumferentially arrayed about the spine, and an outer surface comprising a plurality of electrical elements and polymer material, the plurality of electrical elements arrayed on the spine and electrically connected with the plurality of conductors, the plurality of electrical elements exposed on the outer surface in a pattern, wherein the pattern is different for each lead of the plurality of lead ends, selecting a lead body from a plurality of different lead bodies, each of the different lead bodies having a different length, and connecting the selected lead end with the selected lead body by making mechanical and electrical connections between a plurality of electrical wires of the selected lead body and the plurality of conductors of the selected lead end.

The details of one or more examples are set forth in the accompanying drawings and the description below. Other features, objects, and advantages will be apparent from the description and drawings, and from the claims.

BRIEF DESCRIPTION OF THE FIGURES

FIG. 3 illustrates a spine with ring electrodes.
FIG. 4 illustrates a ring electrode and a conductor.
FIG. 5 illustrates a ring electrode and a conductor.

DETAILED DESCRIPTION OF THE INVENTION

Figure 1:
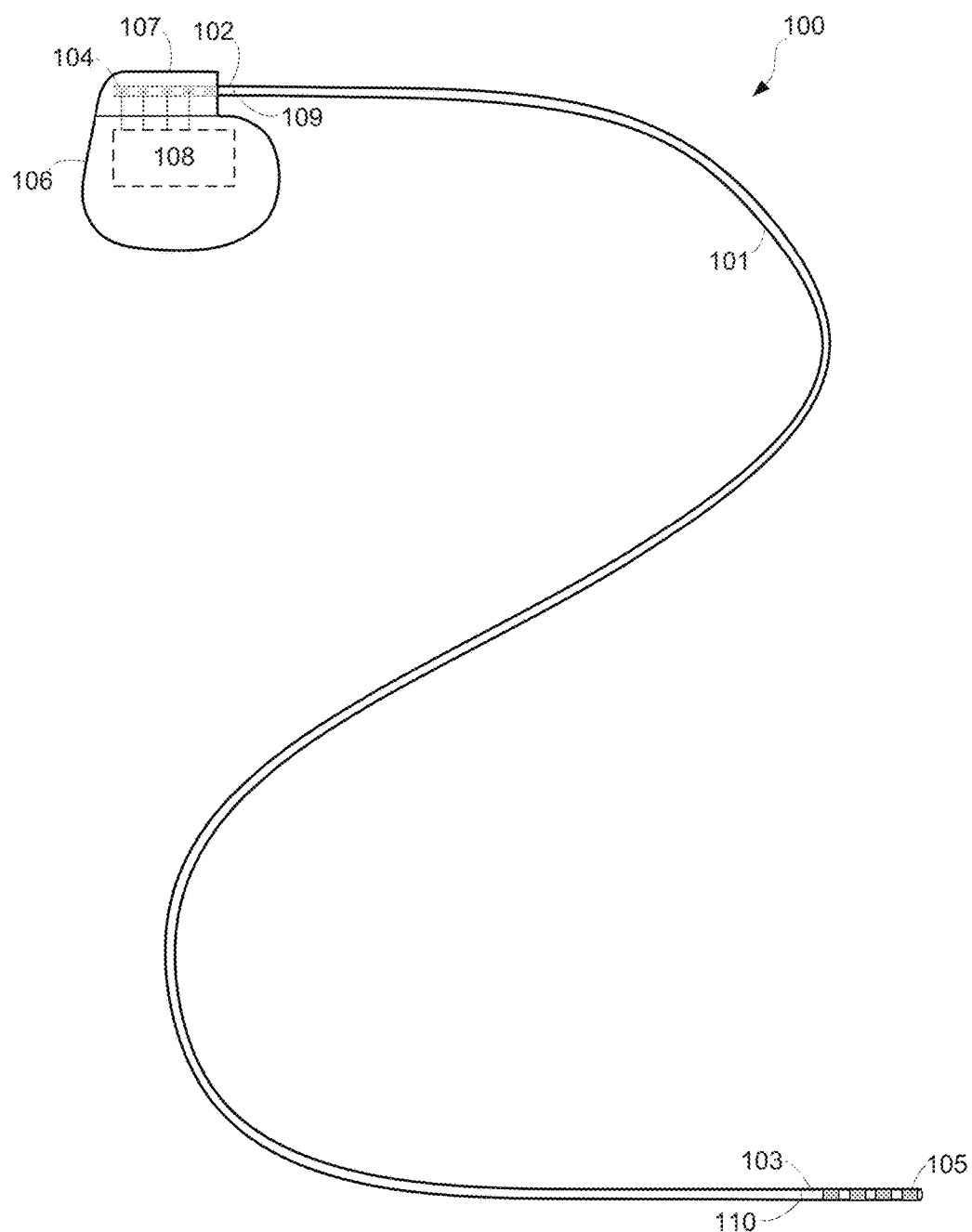
FIG. 1 illustrates an implantable modular lead and an implantable device for one or both of sensing signals and delivering stimulation.

FIG. 1 illustrates an implantable lead 100 plugged into an implantable medical device (IMD) 106. The lead 100 includes a main lead body 101 between a proximal lead end 102 and a distal lead end 103, the main lead body 101 separated from the proximal lead end 102 by seam 109 and the main lead body 101 separated from the main lead body 101 by seam 110. A number of electrodes are on the distal lead end 103 (such as ring electrode 105) while a number of contacts are on the proximal lead end 102 (such as contact ring 104). A plurality of wires, which are not shown in FIG. 1 because they are fully contained within the body of the lead 100, electrically connect respective contacts of the proximal lead end 102 with electrodes of the distal lead end 103. The wires may be in the form of coils, cables, or any other elongated conductor of electrical energy.

The IMD 106 can be configured for stimulating tissue (e.g., as a brain stimulator, spinal stimulator, peripheral nerve stimulator, pelvic nerve stimulator, cardiac stimulator, muscle stimulator, or any other type of stimulator configured to deliver electrical energy). The IMD 106 may additionally or alternatively be configured to sense one or more bioelectrical signals received by one or more electrodes and conducted through the lead 100 (e.g., nerve signals, local field potential signals, brain signals, cardiac signals, electromyogram signals, or any other physiologic signals).

When the proximal lead end 102 of the lead 100 is plugged into the header 107 of the IMD 106, electrical connections are made between conductors of the lead 100 and circuitry 108 of the IMD 106. Circuitry 108 may include signal processing circuitry, stimulation circuitry, a controller, memory, a power source, and/or a switch matrix, among other things. The electrical connections between the IMD 106 and the lead 100 are made by metal conductors within the header 107 of the IMD 106 touching respective contacts (e.g., contact 104) of the proximal lead end 102. At least part of the proximal lead end 102 is inserted into the header 107 to make the physical connections between the contacts of the lead 100 and the conductors of the IMD 106. The exposed contacts of the proximal lead end 102 are spaced to physically align and connect with different metal conductors within the header 107, each of the different metal conductors of the header 107 electrically connecting with different stimulation and/or sensing channels of the IMD 106.

The header 107 includes at least one opening to allow insertion of the proximal lead end 102 into the header 107. In various embodiments, the opening is only slightly larger in diameter then the proximal lead end 102 to minimize the amount of space for bodily fluids to enter the header 107. Furthermore, one or more seals can be located within the header 107, around the proximal lead end 102, to limit bodily fluids from shorting electrical circuits. Electrical signals are conducted between the header 107 and circuitry 108 by a feedthrough that bridges between the housing of the IMD 106 and the header 107.

The main lead body 101 of the lead 100, which is between the proximal lead end 102 and the distal lead end 103 of the lead 100, is relatively flexible to allow the lead 100 to be implanted along curved paths within the body. Furthermore, flexibility of the main lead body allows the lead 100 to accommodate the movements of the body (e.g., along the neck or the back of a patient).

Various leads can have different configurations. For example, the distal lead end 103 may have a particular pattern of exposed electrodes, the pattern based on the shapes of the electrodes (e.g., ring electrodes, segmented electrodes), number of electrodes, the length of each electrode along the distal lead end 103, and/or the spacing between electrodes on the distal lead end 103, among other aspects of electrode configuration. Different electrode configurations can be suited for different stimulation and/or sensing applications. For example, a large number of electrodes widely spaced along the distal lead end 103 may be suited for spinal cord stimulation to address chronic pain as this electrode pattern may provide many options for different programmable stimulation patterns over a large area. A smaller number of electrodes having less spacing may be more appropriate for some deep brain stimulation or for some peripheral nerve stimulation applications. Even within a particular medical application, such as spinal cord stimulation, doctors may have preferences for different electrode configurations. Likewise, the contact pattern on the proximal lead end 102 can vary in contact shape, number, length and/or spacing from embodiment to embodiment. For example, the contact pattern on the proximal lead end 102 may vary depending on which type of IMD 106 is to be used and the different electrical connection configurations within the headers 107, the corresponding number of electrodes on the distal lead end 103.

The main lead body 101 can have different configurations depending on the application for which the lead 100 is intended. The length of the main lead body 101 may be different to accommodate patients of different sizes. Also, the length of the main lead body 101 may be different for different therapeutic and/or monitoring applications.

The different options between the configurations of the main lead body 101, the proximal lead end 102, and the distal lead end 103 means that a lead assembly operation may be tasked with producing a large variety of different lead-types. Leads are often designed and built as a whole unit practically continuous from the proximal end to the distal end. The lead 100 of FIG. 1, however, is a modular lead with the proximal lead end 102 being attached to the main lead body 101 at seam 109 and the distal lead end 103 being attached to the main lead body 101 at seam 110. Lead modularity can simplify the designing and building of a large variety of lead-types. For example, instead of designing and building a great number of different types of leads, some of which may have relatively small variations in length of electrode pattern, lead modularity can allow the design and building of a relatively small number of modular lead parts that can be selected for building a large variety of different lead-types.

The present disclosure concerns, among other things, implantable leads having at least one modular end that is built around a spine. A modular lead is a lead where at least one of the ends of the lead is built separately from the main lead body and is joined to the main lead body after the lead end has been fully or mostly constructed. In some embodiments, lead ends having different configurations (e.g., electrode patterns) can all be attached to a particular type of main lead body. In some embodiments, main lead bodies having different configurations (e.g., different main lead body lengths) can all be attached to a particular type of lead end. In some embodiments, lead ends having different configurations can all be attached to main lead bodies having different configurations. As such, an assembly operation can build lead ends of different configurations and main lead bodies of different configurations and complete assembly of the modular leads by combining the particular lead ends and main lead bodies as needed.

Modularity can have several advantages. In some cases, modularity can alleviate a need to fully construct all different combinations of lead ends and main lead body designs. For example, it may require fewer resources to make main lead bodies of different configurations and lead ends of different configurations that are all able to be connected with one another. As a final or near-final assembly step, the main lead bodies and modular lead ends can be put together depending on which types of final leads are needed. In some cases, if one type of lead end can be attached to different types of main lead bodies, and one type of main lead body is in short supply, then the lead ends of the particular type can be attached to a suitable type of main lead body that is in greater supply. In some cases, having the customizable options of lead ends having different configurations that can all be attached to main lead bodies having different configurations can provide a greater number of options using fewer resources than qualifying and stocking supplies for fully making each of the different lead configurations.

It is further noted that separate construction of lead ends allows the lead ends to be constructed in a different manner then the main body or other components of a lead. A modular lead end constructed separately from the main body can be subjected to processing steps that might be damaging to the main body. For example, a modular lead end can be made by additive lithography methodology or fired in a furnace for ceramic processing or other treatment process. Once constructed and processed separately, the modular lead end can be connected with the main body.

A modular lead end can be built around a spine. A spine can facilitate the consistent construction of lead ends and provide for making a modular connection to a main lead body. A spine can facilitate quick and accurate placement of electrical elements, such as contacts and electrodes, at pre-spaced locations when constructing a modular lead end.

In some cases, the electrode or contact pattern on a lead end (e.g., the number and spacing of electrodes) is based on the configuration of a spine. As such, the configuration of a spine, as further described herein, can determine the pattern of exposed electrical elements defining an outer surface of a lead end.

In some cases, both of a proximal lead end and distal lead end of a lead will be connectable to a main lead body by a modular connection. In some other cases, a proximal lead end of a lead will be a modular lead end but the distal lead end will not be modular and instead will be constructed as part of the main lead body. In some other cases, a distal lead end of a lead will be a modular lead end but the proximal lead end will not be modular and instead will be constructed as part of the main lead body.

FIGS. 2-19 show various aspects for forming a modular lead end and making a modular lead. The modular lead ends being formed in these Figures may correspond to the proximal lead end 102 and/or distal lead end 103 of lead 100, however not all embodiments are so limited.

Figure 2:
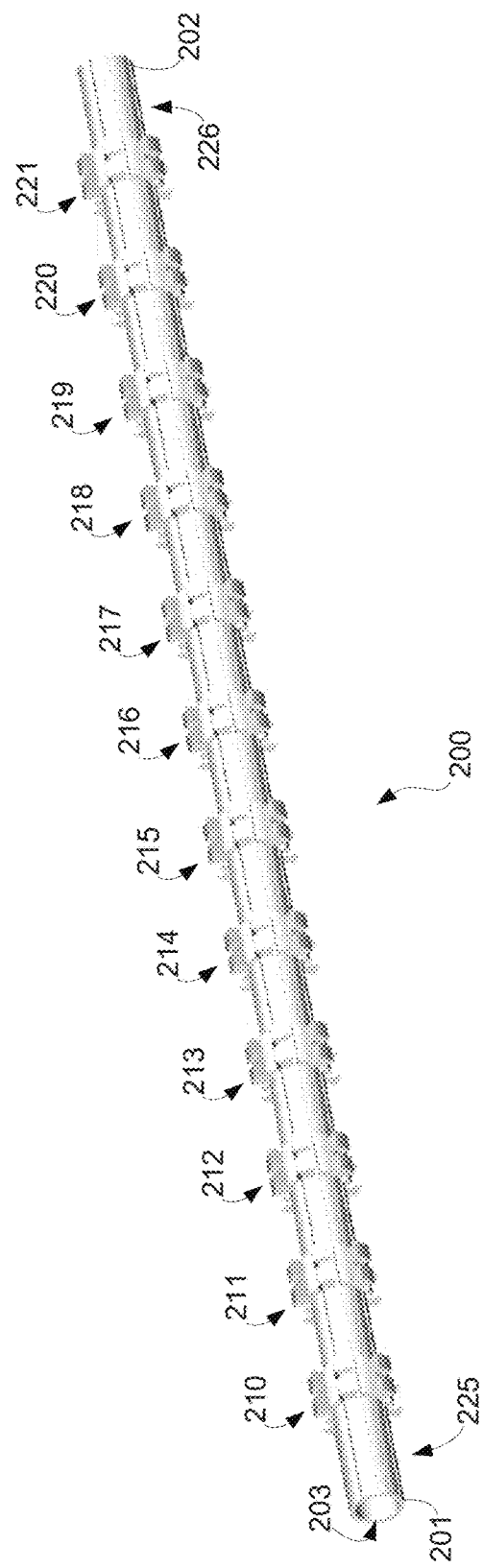
FIG. 2 illustrates an embodiment of a spine.

FIG. 2 illustrates a spine 200. The spine 200 is an elongated structure having a length. The spine 200 has a proximal end 201 and a distal end 202. In the embodiment of FIG. 2, the spine 200 has a lumen running the full length of the spine 200 as shown by lumen opening 203. In various embodiments, spine 200 may have no lumen or a lumen that only runs a partial length of the spine 200.

Spine 200 has multiple paths that run along the spine 200. Along some sections of the spine 200, the paths are defined by projections framing the path, such as projection sets 210-221. The protections within each projection set 210-221 have spaces between the projections for a conductor to fit between the projections and engage the sides of the projections, as will be shown in later assembly steps. Some areas of the spine 200 have channels that define the paths. For example, proximal section 225 has longitudinal channels within the spine 200, the channels arrayed around the circumference of the spine 200. The channels are aligned with the sections of the paths that run through the projection sets 210-221. The channels also run between the projection sets 210-221 and along the distal section 226. In some embodiments, as in FIG. 2, the channels in the spine 200 also run through the projection sets 210-221.

Any number of paths can be arrayed around a spine in various embodiments, such as one, two, three, four, five, eight, ten, twenty, etc. In various embodiments, paths are evenly arrayed around the periphery of the spine. In various embodiments, electrical elements (e.g., contacts or electrodes) are provided on a lead end in a number equal to the number of paths along a spine within the lead end.

Paths are sized and otherwise configured to accommodate a conductor along the spine 200 following the path. In some embodiments, the paths are deep and wide enough that a conductor can run within a channel without extending out of the top of the channel (e.g., the depth of the channel is greater than the height of the conductor). In some embodiments, a conductor sitting as deeply within a channel as possible will still emerge from the top of the channel. In some embodiments, the depth of a channel changes along the length of the channel.

Spines, such as spine 200, can be made in various ways. In some embodiments the spine is a unitary body. Various spines can be made from one or more materials. In some cases, a spine can be made solely from one type of material, such as a polymer material. In the case of a polymer spine, the spine can be formed in the same or comparable shape as shown in FIG. 2 by injection molding or stereolithography. In some cases, a more generalized shape can be formed and then the shape can be machined, cut, or otherwise sculpted to form a desired shape, such as that of the spine 200 shown in FIG. 2. For example, a tube or rod shape can be injection molded or extruded and then machined to form the spine 200 of FIG. 2. A spine can be made from polyether ether ketone (PEEK), polysulfone, polyurethane, and/or another polymer.

Electrical elements can be loaded onto the spine 200. Electrical elements, as referred to herein, are metal lead components exposed on the exterior of a lead (when fully constructed) that are configured for receiving electrical energy into the lead and/or delivering electrical energy from the lead. Electrical elements include, but are not limited to, electrodes and contacts, such as ring electrodes, contact rings, segmented electrodes, segmented contacts, and partial rings.

FIG. 3 shows a portion of the length of the spine 200 onto which ring electrodes 236-238 have been loaded. Each of ring electrodes 236-238 can be placed onto the proximal end 201 or distal end 202 of the spine 200 shown in FIG. 2 and slid to a respective position over one of the projection sets 216-218. As shown in FIG. 3, projection set 216 supports ring electrode 236 in place over the spine 200. Projections can contact the ring electrode 236 to prevent the ring electrode 236 for moving in one or more dimensions. For example, outward projection 204 of the spine 200 is engaged with inward projection 205 of ring electrode 236. This engagement can keep the ring electrode 236 from moving any more proximally and can further center the ring electrode 236 in axial alignment with the spine 200. Ring electrode 236 can have more inward projections around the inner periphery of the ring electrode 236 and the projection set 216 can have more outward projections around the periphery of the spine 200 for respective engagement and stabilization of the ring electrode 236. Likewise, each of the ring electrodes 236-238 can have similar engagement with projections of projection sets 216-218 for positioning and stabilization of ring electrodes 236-238.

The projections within each projection set 215-218 can extend outward different distances. For example, projection 204 projects higher than projection 206. Projection 204 is too high to allow the inner projection 205 of the ring electrode 236 to pass over. However, the shorter projection 206 can serve as a track for the inward projection 205 of the ring electrode 236 to pass over before the ring electrode 236 is rotated to place the inward projection 205 behind projection 204 to seat the ring electrode 236 in place as shown. In some embodiments, ring electrodes (or other types of electrical elements) having inward projections can pass over projections sets only in certain orientations and then can lock in place only at pre-determined locations. In this way, spine 200 can facilitate the assembly of a modular lead end with consistent placement and spacing of electrical elements conforming to a pre-determined pattern by only permitting ring electrodes to track along the spine and lock at particular locations and orientations. The locations and orientations of the electrical elements can correspond to an electrode or contact pattern of a particular type of modular lead end. As such, different spines can have different patterns of outward projections corresponding to different patterns of contacts or electrodes, and the different spines can be individually selected for the construction of a lead end depending on which contact or electrode pattern is desired.

FIG. 3 illustrates conductors 250-254 within paths of the spine 200. As shown in FIG. 3, separate paths are formed between projections within each of the projection sets 215-218. In this way, each of the conductors 250-254 can be held in place along the spine 200 by being within a respective path between projections of the projection sets 215-218. Furthermore, conductors can be arrayed around the circumference of the spine 200 at different angular orientations by being placed within respective paths.

Conductor 250, as with the other conductors along the spine 200, includes a feature 222. Feature 222 comprises an upward bend in the conductor 250. The feature 222 can serve multiple purposes. In the embodiment of FIG. 3, the feature 222 projects outward enough to engage with the edge of the ring electrode 237 while the conductor 250 runs beneath ring electrode 236 (and any other proximal electrode rings). The engagement prevents the conductor 250 from moving any more distally. Also, the conductor 250 may be prevented from moving too far proximally as the feature 222 would engage with ring electrode 236 if it moved proximally. The upward projecting feature 222 can also bring the distal end of the conductor 250 to the edge of the ring electrode 237 for welding between the ring electrode 237 and the conductor 250 to mechanically and electrically connect the ring electrode 237 and the conductor 250. Conductor 251 also includes a feature 223 engaged with the edge of ring electrode 238 which can be welded together. In some cases, the conductors will engage with slots in the electrical elements, such as a slot in a contact ring. Other electrical elements arrayed along a spine can likewise be electrically connected to conductors.

In some cases where the conductors 250-254 are bent upward, as with features 222 and 223, it may be necessary to alternate loading ring electrodes and conductors onto the spine 200. For example, ring electrode 238 can be placed on the spine 200 over projection set 218, and then conductor 251 can be placed on the spine 200 within a particular path as shown with feature 223 abutting the ring electrode 238. Then ring electrode 237 can be placed on the spine 200 over projection set 217 and over conductor 251, and then conductor 250 can be placed on the spine within a particular path with feature 222 abutting the ring electrode 237. This can be repeated for each of the ring electrodes (or other electrical elements) and conductors until the spine 200 is fully loaded with spaced electrodes. The conductors may be welded or otherwise electrically connected to the electrodes as each is loaded onto the spine or once the spine 200 is fully loaded with electrodes. In some alternative embodiments, conductors are mechanically and electrically attached to electrical elements (e.g., ring electrodes) by crimping, such as with a crimp sleeve. A crimp sleeve may be integrated into an electrical element or may be welded to the electrical element.

FIG. 4 illustrates a ring electrode 238, a conductor 250, and a coupling feature 249, all of which can be formed from conductive metal. As shown in FIG. 4, a circular end of the ring electrode 238 can match up with the circular end of the coupling feature 249. The ring electrode 238 can be electrically and mechanically connected to the conductor 250 by welding at and/or along the match up of the circular end of the ring electrode 238 and the circular end of the coupling feature 249.

FIG. 5 also illustrates the ring electrode 238, coupling feature 249, and conductor 250 in an alternative arrangement where the conductor 250 is run through the ring electrode 238 to match up circular ends of the ring electrode 238 and the coupling feature 249 for welding or other technique for electrically and mechanically attaching the ring electrode 238 to the conductor 250. The subassembly of FIG. 4 or FIG. 5 can be loaded onto the spine 200 of FIG. 3 as an alternative way to load the spine 200 with conductors and ring electrodes.

Figure 6:
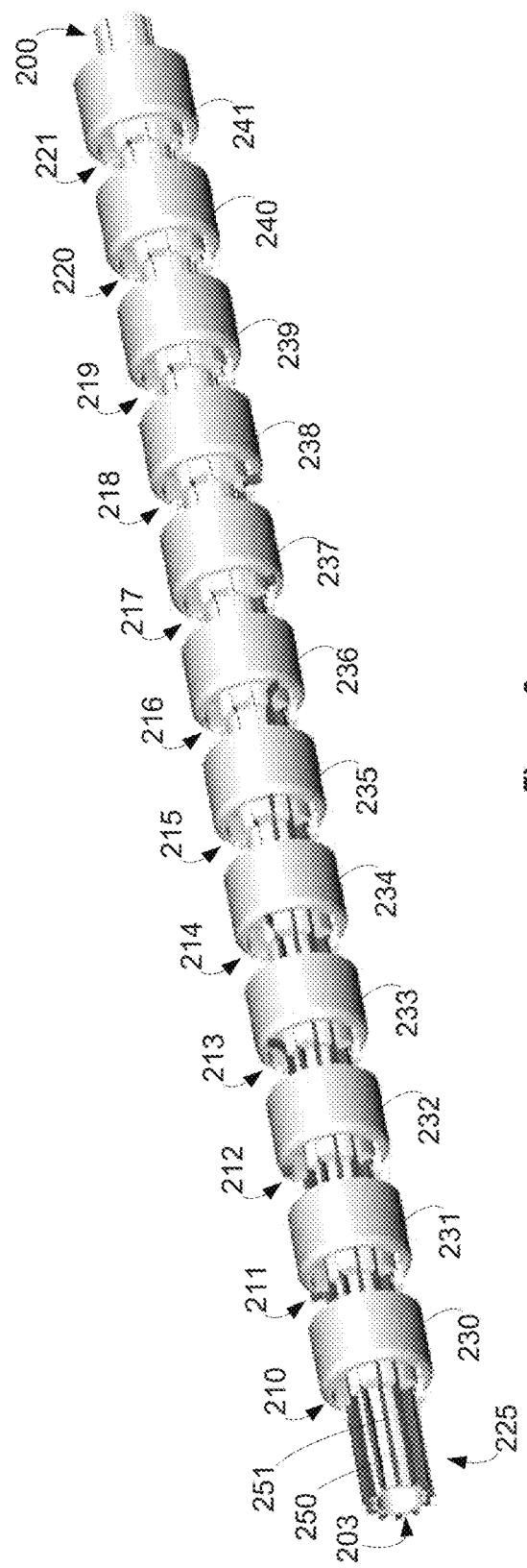
FIG. 6 illustrates a spine loaded with ring electrodes.

FIG. 6 shows spine 200 having been fully loaded with ring electrodes 230-241. Each of the ring electrodes 230-241 is electrically connected to a respective conductor (e.g., conductors 250-254 identified in FIG. 3 being electrically connected to ring electrodes 237-241). The conductors are also arrayed around the proximal section 225 of the spine 200. The conductors can be evenly spaced around the periphery of the proximal section 225. In some embodiments, the conductors can be partially within channels defining the paths of the spine 200 along the proximal section 225, the channels arrayed around the proximal section 225.

Each of the conductors can be a different length. The different lengths can correspond to which electrical elements the conductors will be respectively connected. For example, the length to which each conductor is cut before being loaded onto the spine 200 can be based on to which ring electrode the conductor is to be connected, based on to which projection set the conductor will extend, and/or based on along which path the conductor will be placed. As shown in FIG. 6, the conductors all terminate proximally at the same longitudinal position. That is, the proximal ends of the conductors are aligned with the proximal end of the proximal section 225, and because each conductor connects with a different electrode ring at a different longitudinal position along the spine 200, each of the conductors is a different length.

As shown in FIG. 6, alignment of ring electrodes 230-241 by placement over the projection sets 210-221 of the spine 200 provides for an array of ring electrodes 230-241 evenly spaced along the spine 200. Specifically, the array of ring electrodes 230-241 has consistent spacing between the ring electrodes 230-241. Also, stabilizing the ring electrodes 230-241 over the projection sets 210-221 can axially align each of the ring electrodes 230-241 with each other and with the spine 200. There is some clearance between the inner surfaces of the ring electrodes 230-241 and the outer surface of the projection sets 210-221. Enough clearance is provided to allow the ring electrodes 230-241 to slide over the spine 200. In some cases this clearance also allows polymer fill to penetrate and fill the space between the inner surfaces of the ring electrodes 230-241 and the outer surfaces of the projection sets 210-221, as will be later described. In various embodiments, the clearance between the inner surfaces of the ring electrodes 230-241 and the outer surface of spine 200 is small enough to keep the ring electrodes 230-241 substantially axially aligned with each other and the spine 200 by some contact between the inner surfaces of the ring electrodes 230-241 and the outer surfaces of the projection sets 210-221. Axially aligned ring electrodes 230-241 provide a consistent and smaller profile as the proximal lead end 102 or distal lead end 103 of FIG. 1, for example. A smaller and smoother profile can facilitate plugging a proximal lead end into an opening of a header. Moreover, axially aligned ring electrodes 230-241 can provided for tighter tolerances with seals of the header to keep fluids out of the header and from further penetrating between contact rings within the header.

It is noted that the conductors arrayed around the proximal section 225 have a patterned relationship with the ring electrodes 230-241 positioned along the spine 200. Specifically, the angular positions of the conductors around the spine 200 correspond with the longitudinal positions of the ring electrodes 230-241. For example, conductors that are adjacent around the spine 200 electrically connect with ring electrodes 230-241 that are adjacent along the spine (except for the ring electrodes 230 and 241 at the proximal and distal ends of the spine 200). For each conductor around the proximal section 225 electrically connected with a ring electrode, the adjacent conductor in the clock-wise direction around the proximal section 225 will electrically connect with the adjacent ring electrode in the distal direction along the spine 200. As shown in FIG. 6, conductor 250 electrically connects with ring electrode 234. Conductor 251, which is adjacent and clockwise relative to conductor 250, electrically connects with ring electrode 235, which is adjacent and distal of ring electrode 234. This relationship of course only exists for the ring electrodes in a row and two adjacent conductors around the proximal section 225 will electrically connect with the most proximal ring electrode 230 and the most distal ring electrode 241.

A core pin (not illustrated) can be placed within the lumen of the subassembly shown in FIG. 6. Specifically, a metal pin can be inserted through the lumen opening 203 of the spine 200 partway or all of the way through the lumen. This subassembly, with the core pin, can be placed within a cavity of an injection mold die (not illustrated). The cavity can define a negative of a cylindrical lead end. For example, the cavity can define a negative of the distal lead end 103 of the lead 100 of FIG. 1. The inner diameter of the cavity can be slightly larger than the outer diameter of the ring electrodes 230-241, sufficient to accommodate the ring electrodes 230-241 within the cavity. The inner diameter of the cavity can be small enough to prevent polymer fill from flashing over the ring electrodes 230-241 by fitting closely over these components. The inner diameter of the cavity can be narrower along the proximal section 225, the inner cavity being slightly larger than the outer edges of the conductors arrayed along the proximal section 225.

When the die of the injection mold is closed, such as by two plates coming together, molten polymer fill (e.g., polymer resin heated to allow the polymer material to flow) can be injected to fill in the cavity. The polymer fill can fill the entire space of the cavity thereby surrounding many of the components of the subassembly. Once the injection of polymer fill is complete the die can be cooled, the polymer material solidifying as it cools. The subassembly can then be removed from the injection molding die. Gates from injection molding can be cut from the subassembly.

Figure 7:
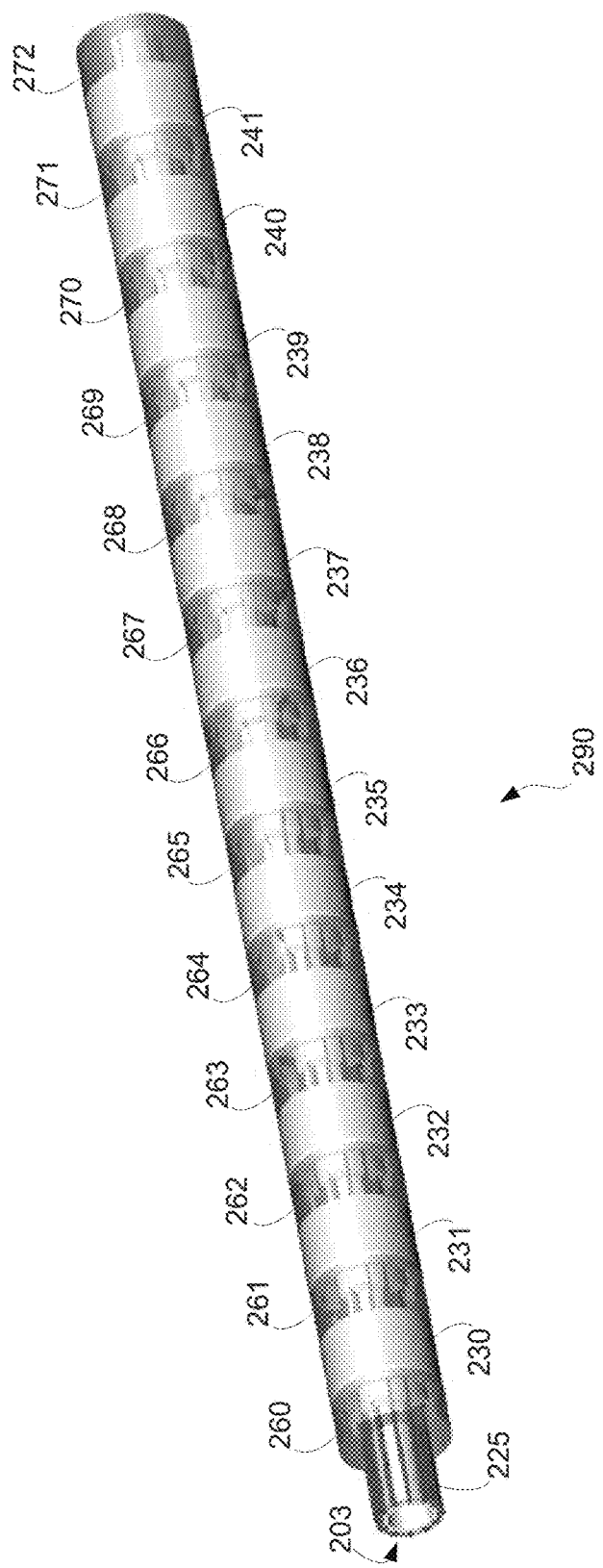
FIG. 7 illustrates a modular lead end.

FIG. 7 illustrates a lead end 290 following injection molding as described above and after removal of the core pin. Many of the components of the subassembly of FIG. 6 have been partially or fully encapsulated by polymer fill, such as conductors 250-254, spine 200, and projection sets 210-221. Also, ring electrodes 230-241 have been surrounded and embedded in polymer fill while leaving portions of the ring electrodes 230-241 exposed for receiving and/or delivering electrical energy.

The paths in channels and/or between projections can also be partially or fully filled with polymer fill to allow the polymer fill to mechanically grip the spine 200 and bind the components of the lead end 290, particularly the sections of the paths not occupied by conductors. Also, the spaces between the ring electrodes 230-241 have been filled in with polymer fill. As a result, polymer sections 260-272 have been formed from the inner surface of the die cavity, forming a cylindrical shape that spans between the ring electrodes 230-241. The outer diameter of each of the polymer sections 260-272 is substantially the same as the outer diameter of the ring electrodes 230-241. As such, each of the ring electrodes 230-241 is in direct contact with polymer sections 260-272 proximally and distally. The ring electrodes 230-241 being surrounded proximally and distally by the polymer sections 260-272 fixes the ring electrodes 230-241 in respective positions along the lead end 290, including fixing the axial alignment and spacing between the ring electrodes 230-241.

The polymer fill can encapsulate at least part of the spine 200, mechanically fixing the spine 200 to the other portions of the lead end 290, including the ring electrodes 230-241. In some embodiments the polymer fill will further melt or otherwise chemically bond with the polymer material of the spine 200, however not all embodiments of this disclosure are so limited.

The polymer fill acts as a web of material that is mechanically attached to the components of the lead end 290 by surrounding some or all of the component surfaces. For example, the polymer fill spans underneath each of the ring electrodes 230-241 to bridge between each of the polymer sections 260-272. In various embodiments, the polymer fill will be continuous from the proximal end of the spine 200 to the distal end of the spine 200, thereby fixing the components around the spine 200 and making a robust lead end 290.

The spine 200 adds stiffening strength to the lead end 290 and the polymer fill mechanically binds the components of the lead end while also insulating various components. The section of a lead containing spine 200, such as the lead proximal lead end 102 or lead distal lead end 103 of FIG. 1, can be stiffer than the main lead body 101 because of the presence of the spine 200. In this way, the spine 200 can add stiffness to a section of a lead where it is needed while leaving the remainder of a lead, such as a main lead body 101, flexible for conforming to an implant path in the body and moving with the body. In various embodiments, the section of the lead containing the spine 200 can still flex but will be stiffer than the sections of the lead that do not have a spine 200.

In some embodiments, the spine can be a supportive member adding stiffness to an end of a lead. In some cases, a stiff proximal lead end 102 can more easily overcome obstacles (e.g., seals) resisting insertion, thereby facilitating easier insertion of the proximal lead end 102 into the header 107. A particularly stiff proximal lead end 102 of the lead 100 may be useful in inserting the proximal lead end 102 into the header 107, in case an initial misalignment causes the proximal end to bend while the physician pushes the proximal end. A stiff proximal lead end 102 can also serve has a firm and robust handle for a physician in inserting the proximal lead end 102 into the header 107. Also, a stiff proximal lead end 102 can maintain its integrity during insertion, where a more flexible end may be too floppy or prone to kinking for quickly and confidently inserting the flexible end into the header 107 during an implantation procedure. The spine 200 may be substantially stiffer than conductors (e.g., cables, filars, coils, or other elongated conductive elements) within the lead. As such, in various embodiments, the stiffness of a lead end comes predominantly from the spine 200 as compared to the stiffening contributions of other longitudinally extending components of the lead end.

The polymer fill can be transparent. As shown in FIG. 7, the spine 200 can still be seen beneath the polymer fill forming the polymer sections 260-272. The polymer fill material may be, for example, opaque, colored, transparent, or non-transparent. The polymer fill may be polyether ether ketone (PEEK), polysulfone, polyurethane, and/or another polymer.

Figure 8:
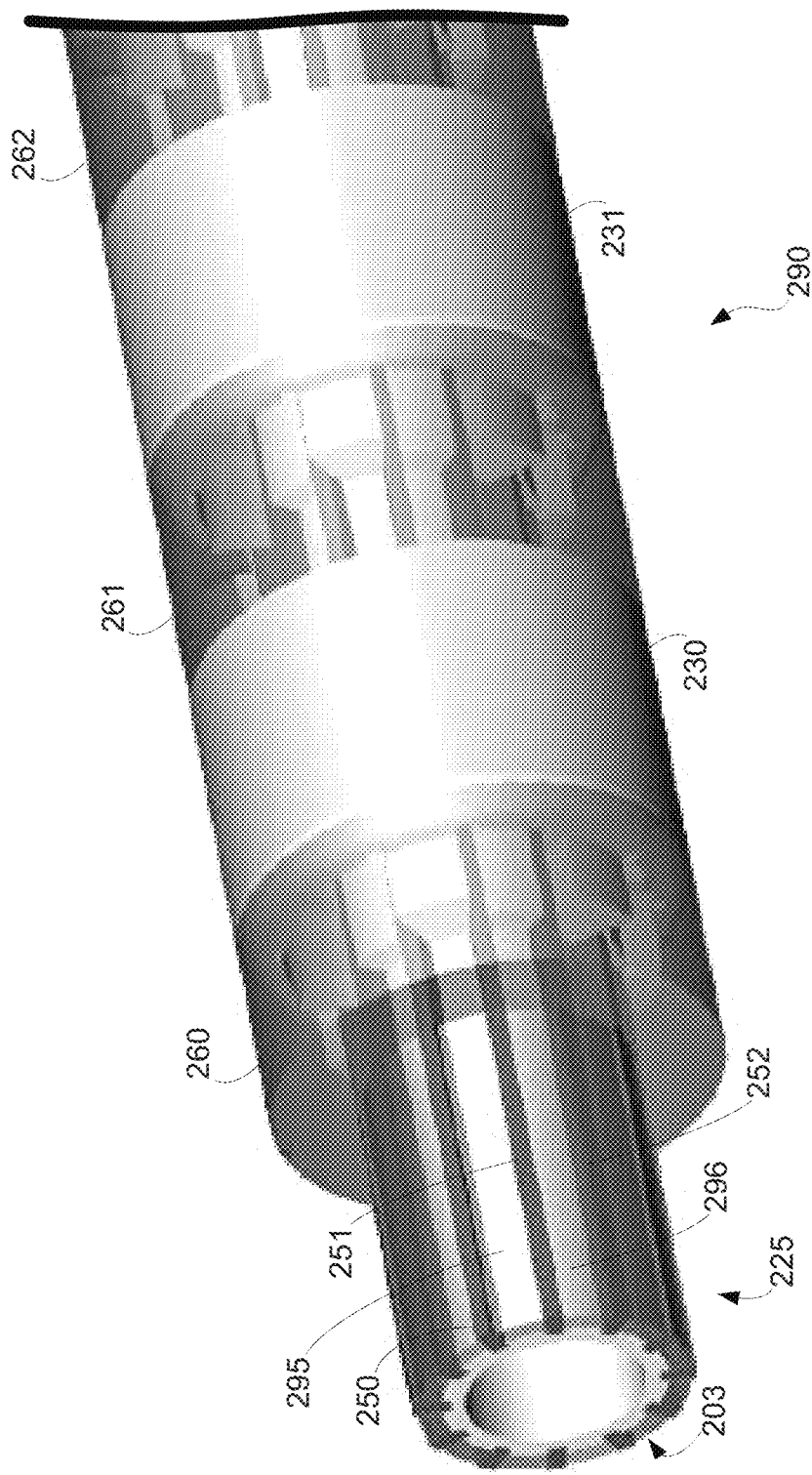
FIG. 8 illustrates a modular connector of a modular lead end.

FIG. 8 shows a closer view of the proximal section 225 of the lead end 290. As shown in FIG. 8, the conductors are arrayed around the circumference of the proximal section 225 of the spine 200 and polymer fill has filled in the spaces between the conductors. Polymer section 295 fills in the space between conductors 250 and 251, from the proximal opening 203 of the lumen to polymer section 260. Also, polymer section 296 fills in the space between conductors 251 and 252, from the proximal opening 203 of the lumen to polymer section 260. In this way, polymer sections, such as polymer sections 295 and 296, surround the periphery of the proximal section 225. These polymer sections can provide further insulation between the conductors along the proximal section 225. In some cases the polymer sections will not extend outward as far as the conductors extend, while in some other cases the polymer sections will extend outward to be even with the conductors around the proximal section 225. In some other cases the polymer sections may extend beyond the conductors such that the conductors are within channels defined by the polymer sections along the proximal section 225.

Figure 9:
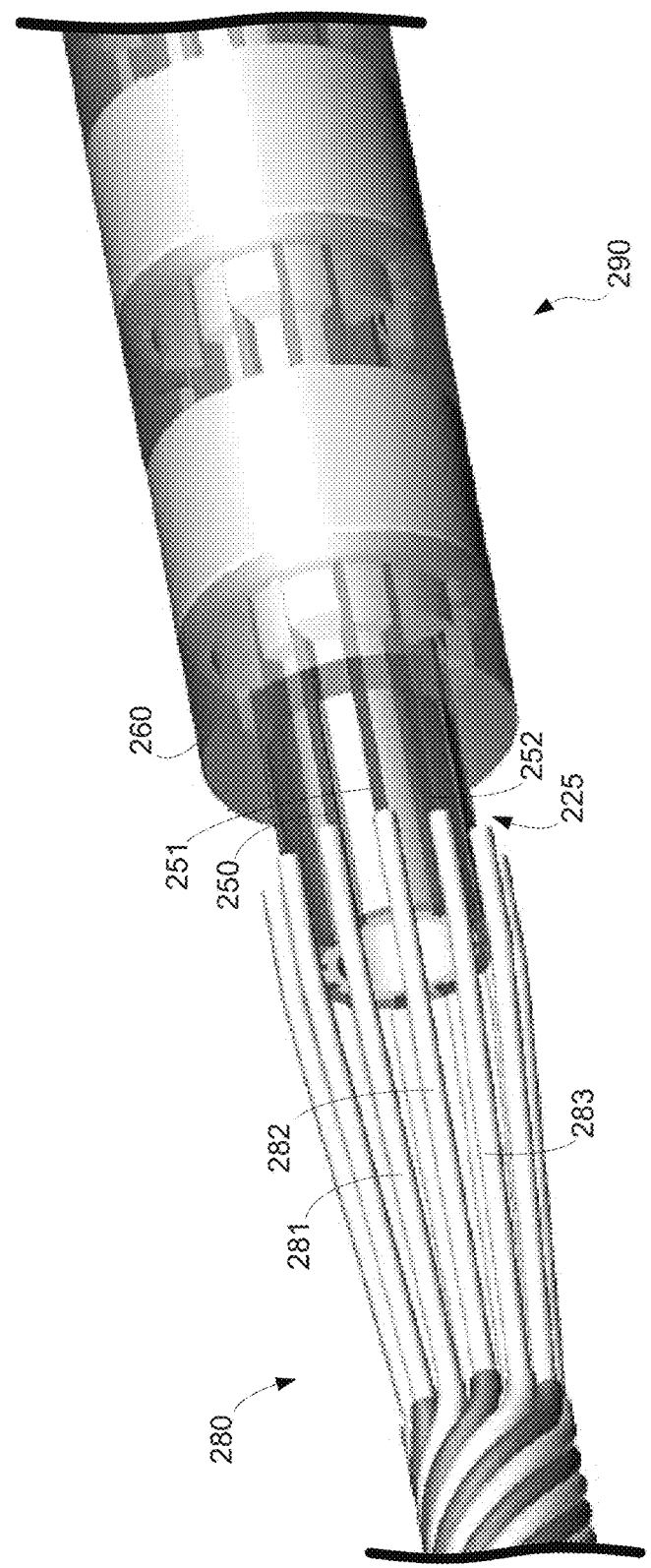
FIG. 9 illustrates connecting a main lead body to a modular lead end.

Lead end 290 is a modular lead end having a modular connector at the proximal section 225 for making a modular connection with a lead main body. The proximal section 225 is configured as a modular connector for connection between respective electrical wires of a main lead body and the conductors of the lead end 290. As opposed to loose or irregularly bundled wires, the conductors of the proximal section 225, such as conductors 250-252, are evenly arrayed around the periphery of the proximal section 225, thereby providing an arrangement of conductors for connecting with electrical wires of a main lead body. FIG. 9 illustrates an arrangement 280 of electrical wires of a main lead body (which could correspond to the main lead body 103 of FIG. 1). The electrical wires of the wire arrangement 280, such as wires 281-283, are splayed in a radial arrangement that aligns individual wires of the wire arrangement 280 with individual conductors of the proximal section 225, as shown in FIG. 9. The wire arrangement 280 can be part of a coil of wires spanning a main lead body, for example.

With the wire arrangement 280 and the conductors of the proximal section 225 aligned, electrical wires and conductors can be welded to one another. For example, with wire 281 overlapping conductor 250, a weld joint can be made between the overlap of wire 281 and conductor 250. Likewise, a weld joint can be made between the overlap of wire 282 and conductor 251, and another weld joint can be made between the overlap of wire 283 and conductor 252. In some embodiments, crimping can be performed in addition to or as an alternative to welding wires to conductors. Welding or other technique for electrically connecting conductors can be continued around the proximal section 225 until each wire of the wire arrangement 280 is mechanically and electrically connected to a respective conductor of the proximal section 225.

The electrical wires of the wire arrangement 280 can run the full length of lead main lead body, such as the main lead body 103 in FIG. 1. The wires of the wire arrangement 280 may be contained within a main lead body tube (not shown) proximally of the lead area shown in FIG. 9. The main lead body tube can, among other things, block bodily fluids from penetrating within the lead where the wires are contained. The main lead body tube may extend from seam 109 to seam 110 in FIG. 1, for example. Likewise, the electrical wires of the wire arrangement 280 may run the full length of the main lead body and be configured to carry electrical energy from one end of the main lead body to the other (e.g., to facilitate electrical connectivity between the contacts of the proximal lead end 102 to the electrodes of the distal lead end 103).

Spine 200 and conductors arrayed around the spine 200 can facilitate accurate and efficient modular connections between a lead end 290 and a main lead body. The angular relationship of the conductors around the spine 200 corresponding with the longitudinal position of the ring electrodes 230-241 can facilitate efficient joining of the lead end 290 and the main lead body while correctly making the intended electrical connections between the electrical wires of the wire arrangement 280 and the conductors of the lead end 290. Otherwise, an assembler joining two bundle of wires and conductors or other collection having no pattern may need to test the wires, conductors, electrode rings, and/or contact rings in a trial-and-error fashion to determine which conductors electrically connect with which electrodes and accordingly which conductors and wires to electrically connect between the lead end 290 and the wire arrangement 280. In the lead end 290, as discussed above, the conductors arrayed around the proximal section 225 already have an angular relationship that corresponds with a positional relationship of the ring electrodes 230-241 along the lead end 290. As such, trial-and-error testing during assembly of leads may be minimized or avoided, making the assembly of leads more efficient, predictable, and accurate. For example, once the electrical connectivity between one conductor and one ring electrode are known, the pattern of the electrical connectivity between the other conductors and ring electrodes can be followed without further testing and/or analysis. If the electrical wires are likewise in a patterned arrangement, then the pattern can be followed for pairing the conductors with particular electrical wires after matching one electrical wire and one conductor for electrical connection.

Once electrical connections have been made between the wires of the main lead body and the conductors of the lead end 290, an exterior of a lead can be formed over the junction between the wire arrangement 280 and the conductors of the proximal section 225. For example, an outer tube can be run over the wires of the wire arrangement 280 from the proximal direction to engage with polymer section 260 and a heat bond can be applied to bond the tube and the polymer section 260. The tube can be the tube spanning the length of the main lead body 103 in FIG. 1, for example. A modular lead end connection in this manner may create a seam, such as the seam 110 of FIG. 1. In some embodiments, the subassembly shown in FIG. 9 may be placed in an injection mold die and polymer fill can be injected to encapsulate the wires of the wire arrangement 280 and the conductors of the proximal section 225 and define a cylindrical lead exterior. These are and other means are contemplated for connecting a modular lead end to a main lead body.

While the above embodiment demonstrates the placement of electrode rings along a spine, other electrical elements may additionally or alternatively be arrayed along a spine in the same or similar manner. An electrical element, as used herein, refers to an electrically conductive component exposed on a lead and configured to deliver electrical energy from the lead and/or receive electrical energy into the lead. Contact rings, ring electrodes, and segmented electrodes are electrical elements, but electrical elements are not necessarily limited in these options. A segmented electrode refers to an electrode that only spans around a limited portion of the circumference of a lead, and in some cases multiple segmented electrodes (e.g., three) are arrayed around the same circumference of a section of a lead. Segmented electrodes, or other electrical elements, may have features such as projections on their underside, where injected polymer fill can encapsulate the features to mechanically attach the segmented electrode to the spine and the rest of the lead end.

Conductor, as referenced herein, can be an individual metal filar, cable, or coil, for example. Conductors as referenced herein can also be elongated bars, such as elongated conductors having square or rectangular outer profiles. Conductors can be relatively stiff or relatively flexible. Conductors as referenced herein can be made of metal or other conductive material and can be configured to conduct electrical energy (e.g., stimulation pulses and/or bioelectrical signals) along a lead end. Each conductor can further be coated (e.g., with polytetrafluoroethylene (PTFE)) to insulate the conductive metal to prevent electrical shorting.

Figure 10:
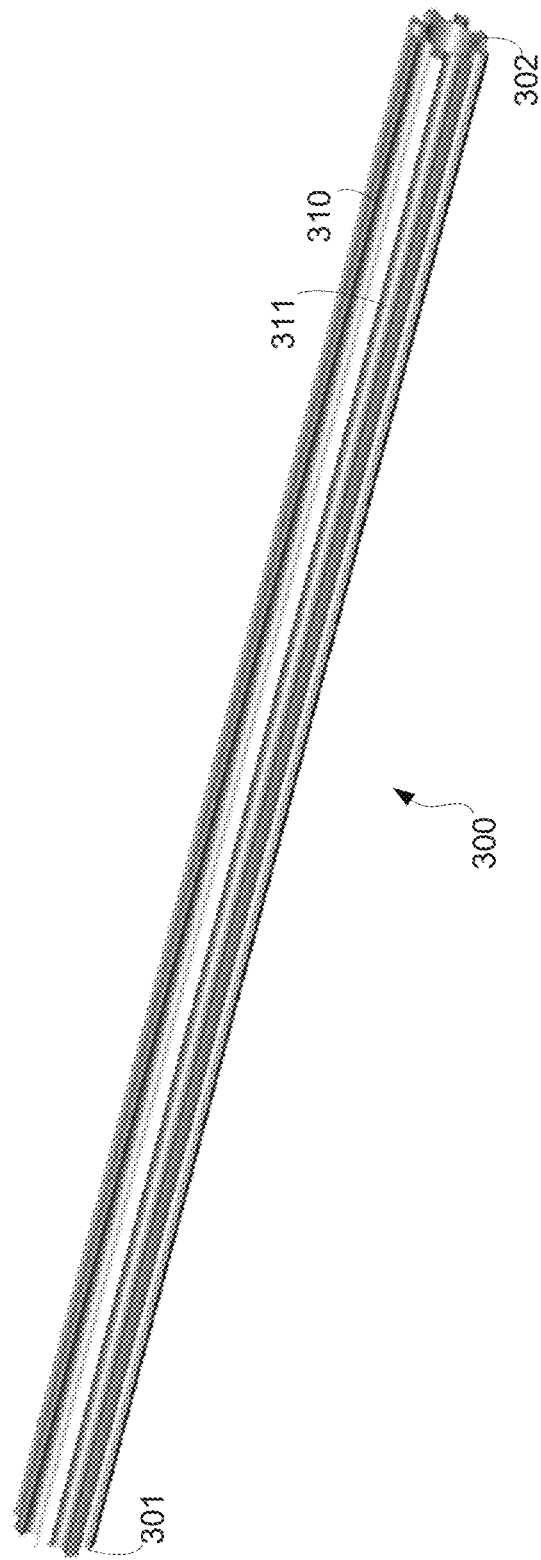
FIG. 10 illustrates an embodiment of a spine.

FIG. 10 illustrates a spine 300. The spine 300 is an elongated structure having a length. The spine 300 has a proximal end 301, a distal end 302 and a lumen running from the proximal end 301 to the distal end 302.

Figure 11:
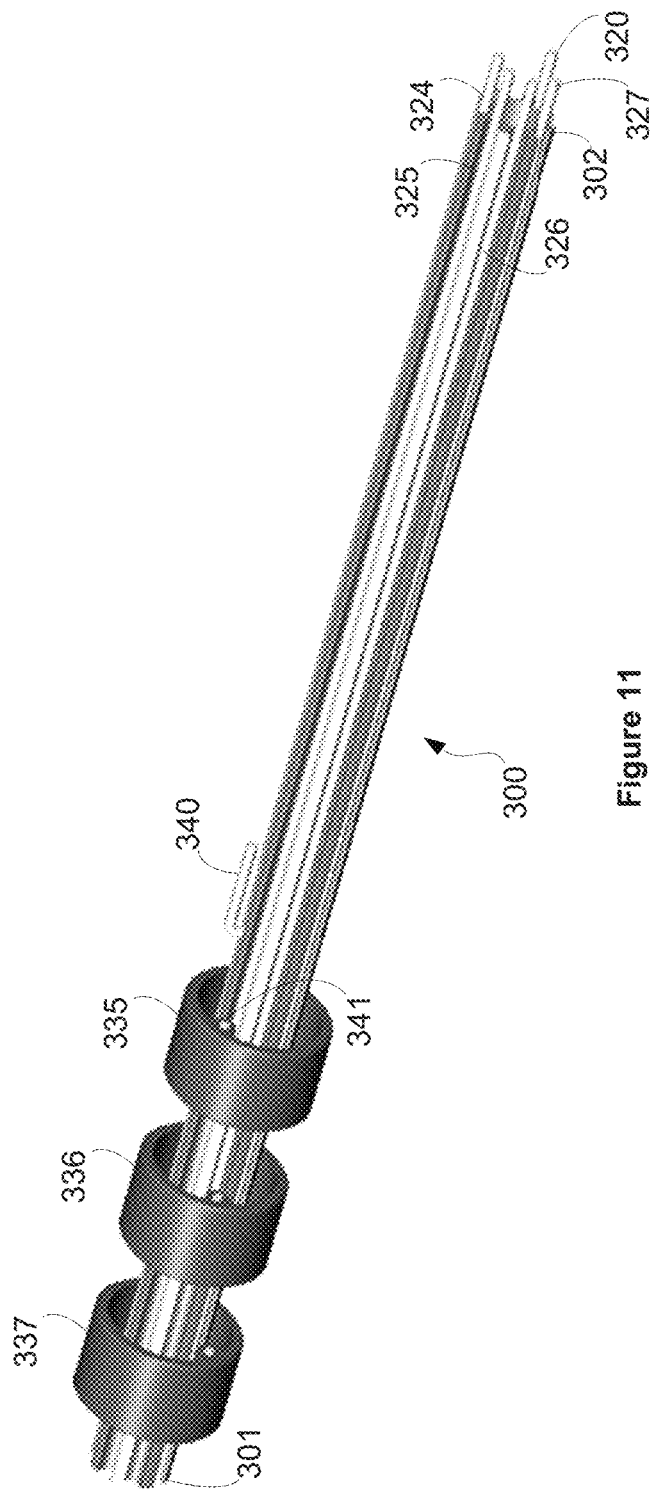
FIG. 11 illustrates a spine with ring electrodes.

Spine 300 has multiple paths that run the length of the spine 300. Each path is in the form of a channel within spine 300, such as paths 310 and 311. Paths could additionally or alternatively be defined by projections or other features. As shown in FIG. 11, each path is sized and otherwise configured to accommodate a conductor along the spine 300. As shown in FIG. 11, conductors 320 and 324-326 are within respective paths of the spine 300.

Electrical elements can be loaded onto the spine 300. For example, FIG. 11 shows contact rings 335-337 loaded onto the spine 300. In each case, a respective conductor is placed in a path and a ring electrode is placed over the distal end 302 of the spine 300 such that the spine 300 goes through each ring. Each conductor has a feature, such as feature 340 on conductor 324. Feature 340 is a bend in the conductor 324 that faces rearward to engage a coupling feature of a contact ring. For example, the feature 341 of conductor 325 is shown extending within the coupling lumen feature of contact ring 335. As such, each contact ring can be slid along the spine 300 and aligned to engage with a feature of a conductor, thereby securing the conductor to the contact ring.

Figure 12:
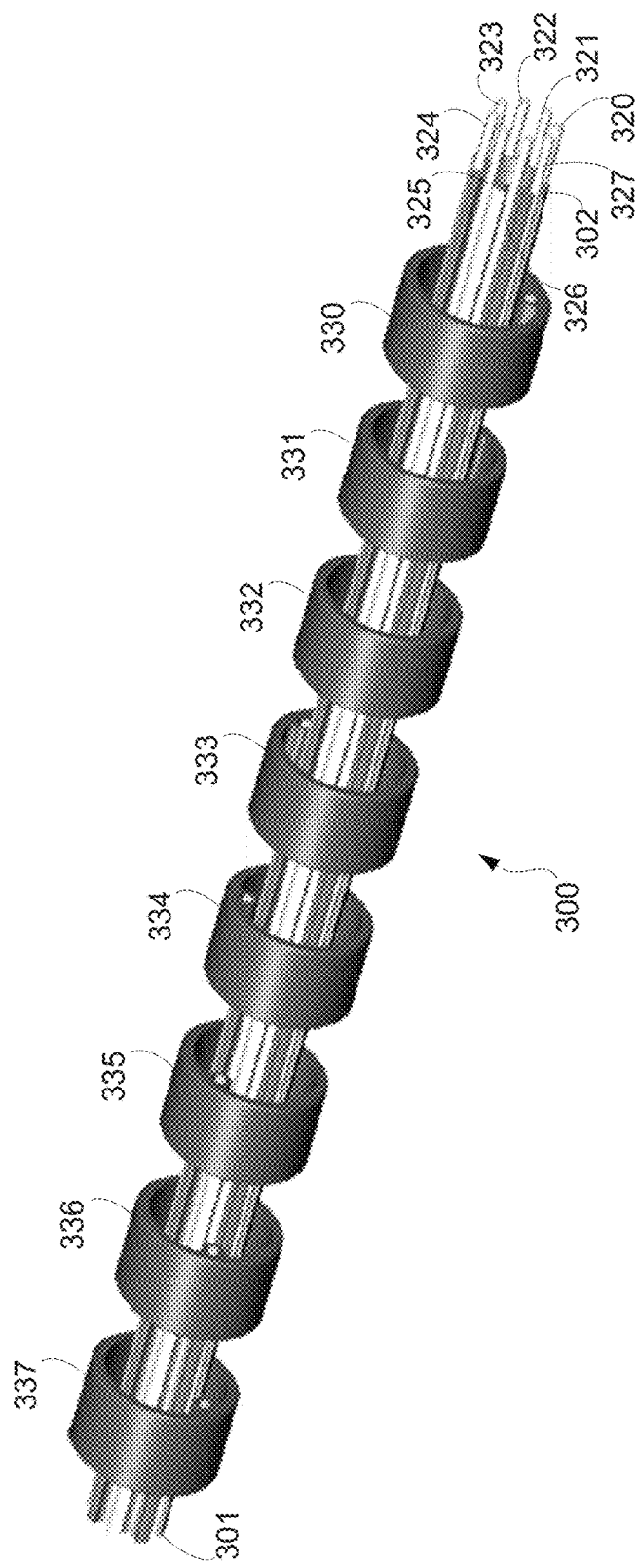
FIG. 12 illustrates a spine loaded with contact rings.

The spine 300 can be loaded by alternating between placing a conductor on the spine 300 and then placing a contact ring on the spine 300 to engage the contact ring with the feature of the conductor. FIG. 12 shows spine 300 fully loaded with contact rings 330-337. The contact rings 330-337 are attached, and thereby electrically connected, to conductors 320-337. As with the subassembly of FIG. 6, the angular position of the conductors 320-337 around the spine 300 corresponds with the longitudinal position of the contact rings 330-337. In particular, conductors 320-337 that are adjacent around the spine 300 electrically connect with contact rings 330-337 that are adjacent along the spine (except for the contact rings 330 and 337 at the proximal and distal ends of the spine 300).

As shown in FIG. 12, the contact rings 330-337 are axially aligned with one another and with the axis of the spine 300 by engagement with the respective conductors 320-337 (e.g., by use of bend features 340-341). Furthermore, the contact rings 330-337 are evenly spaced along the spine 300. The even spacing can be provided by the conductors 320-337 having consistently different lengths, such that alignment of the distal ends of the conductors 320-337 will evenly space the respective features of the conductors 320-337 and the contact rings 330-337 that are engaged with the features.

Use of the spine 300 and conductors 320-337 of different lengths which evenly space contact rings 330-337 along a lead proximal end, or other use of a spine to position electrical elements along a lead end can provide for higher lead reliability. For example, the contacts of the proximal lead end 102 in FIG. 1 should align with the spacing of the metal conductors within the header 107 so that each contact is electrically connected with a different channel of circuitry 108 of the IMD 106. Misalignment due to contact spacing errors on the proximal lead end 102 can cross channels or fail to electrically connect with a proper channel. Likewise, spacing of electrodes on the distal lead end 103 which fails to follow an intended design can compromise sensing and/or stimulation coverage.

Figure 13:
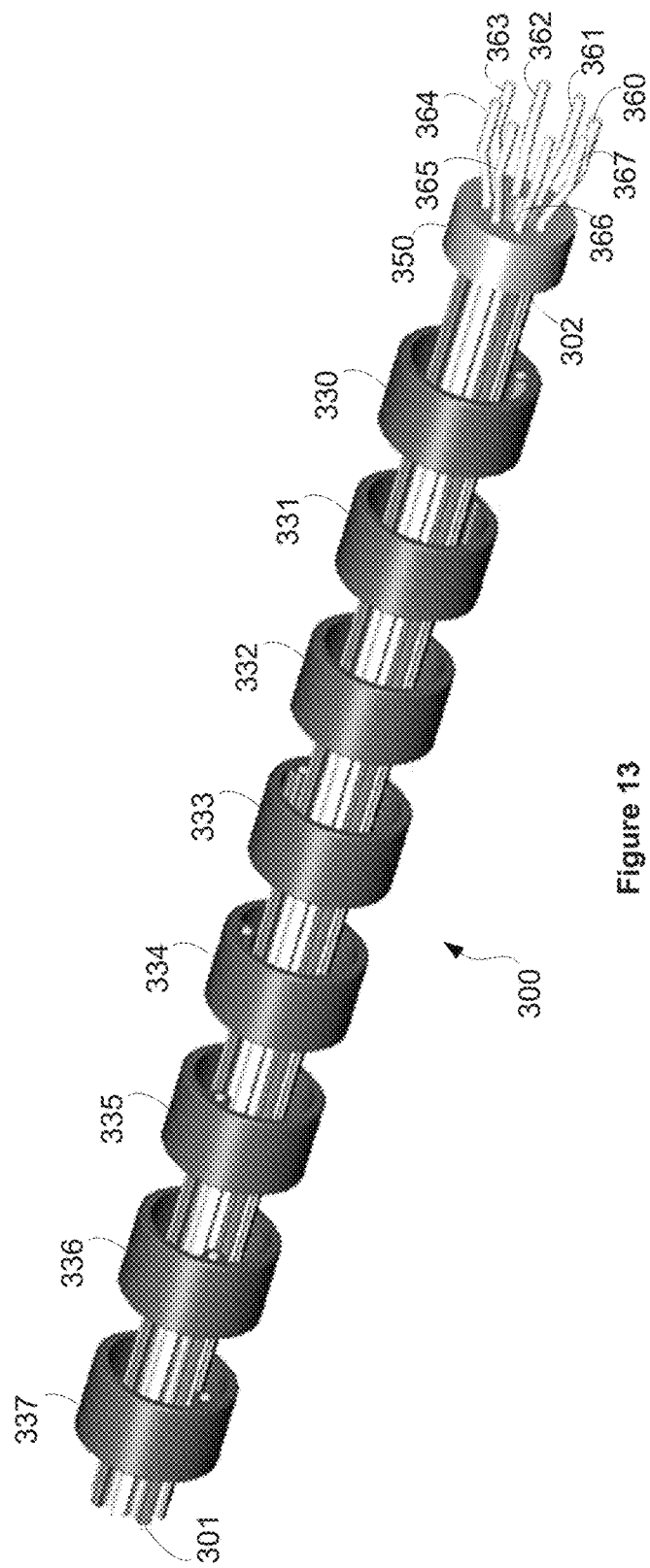
FIG. 13 illustrates a spine loaded with contact rings.

FIG. 13 shows that a divider 350 has been placed on the distal end 302 of the spine 300. The divider 350 is a polymer or ceramic disc having a plurality of holes. A central hole of the divider 350 aligns with the lumen of the spine 300. In some cases, conductors 320-337 can be run through radially arrayed holes in the divider 350 to form the splay of conductors 360-367 shown in FIG. 13. In some embodiments, conductors 360-367 in the splayed arrangement are physically different from conductors 320-337 (identified in FIG. 12) within the paths of the spine 300 but are electrically connected with the conductors 320-337 by physical engagement between the ends of the conductors 320-337 and conductors 360-367 within the divider 350.

A core pin (not illustrated) can be placed within the lumen of the subassembly shown in FIG. 13. This subassembly, with the core pin, can be placed within a cavity of an injection mold die (not illustrated). The cavity can define a negative of a cylindrical lead end. For example, the cavity can define a negative of the proximal lead end 102 of FIG. 1. The inner diameter of the cavity can be slightly larger than the outer diameter of the contact rings 330-337, sufficient to accommodate the contact rings 330-337 within the cavity. The inner diameter of the cavity can be small enough to prevent polymer fill from flashing over the contact rings 330-337 by fitting closely over these components.

Figure 14:
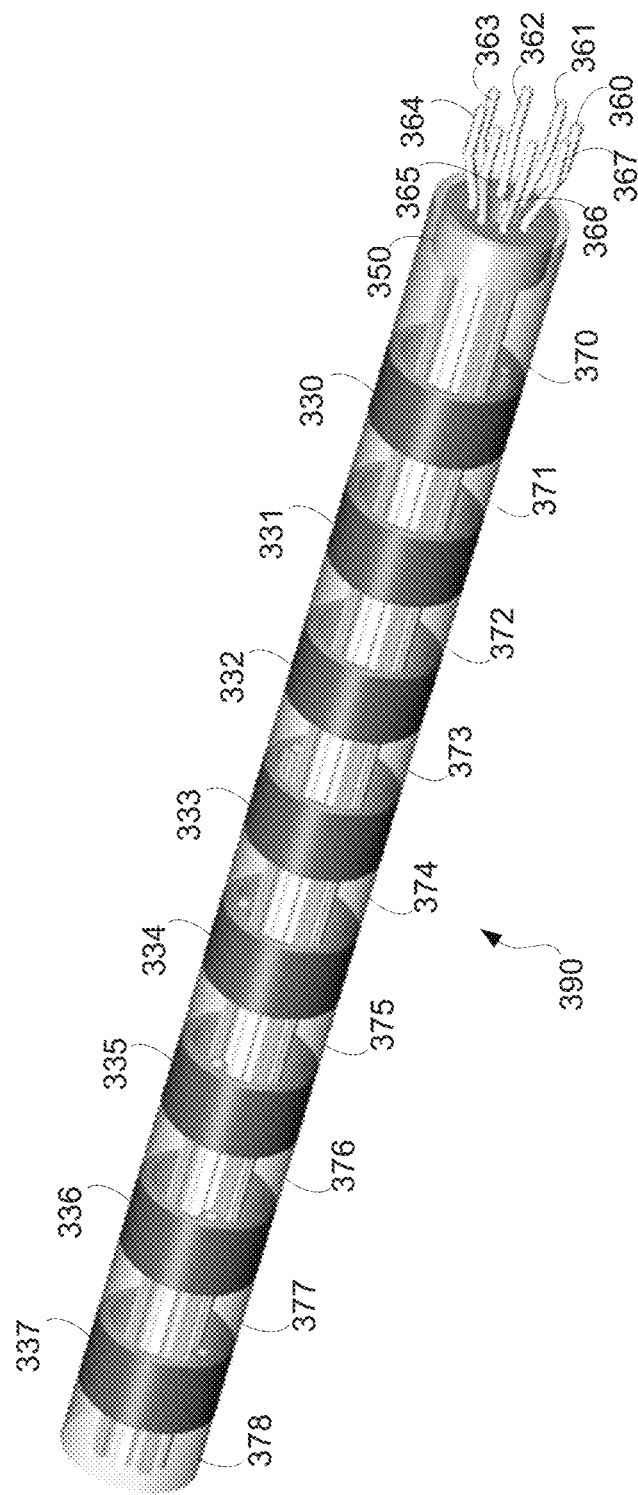
FIG. 14 illustrates a modular lead end.

When the die of the injection mold is closed, such as by two plates coming together, molten polymer fill can be injected to fill in the cavity. The lead end 390 shown in FIG. 14 shows the spaces between the contact rings 330-337 and the divider 350 being filled by polymer fill, making polymer sections 370-378. The polymer fill can encapsulate and mechanically bind lead components as described herein. The divider 350 can be partially or fully encapsulated by the polymer fill and thereby fixed to the other components of the lead end 390. Lead end 390 is a modular lead end having a modular connector at the distal end for making a modular connection with a lead main body. The arrangement of the conductors 360-367 splayed by the divider 350 is configured as a modular connector for connection between respective electrical wires of a main lead body and conductors of the lead end 390, as further shown in FIG. 15.

Figure 15:
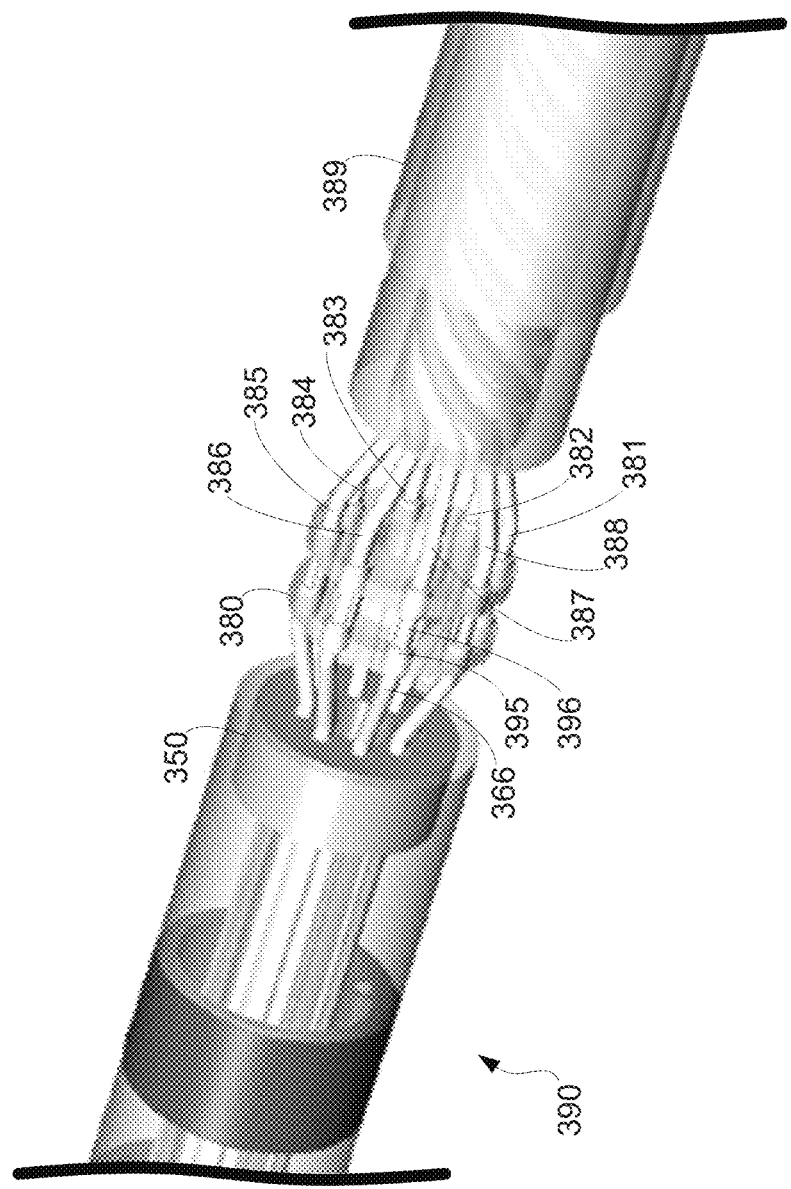
FIG. 15 illustrates connecting a main lead body to a modular lead end with a hub.

The conductors 360-367 in the splayed arrangement may engage with a first side of a hub 380 as shown in FIG. 15. FIG. 15 also shows main lead body 389 containing electrical wires 381-388. The electrical wires 381-388 are positioned in a splayed arrangement and are engaged with the second side of the hub 380. In this way, electrical connections can be made between complementary pairs of the conductors 360-367 and the electrical wires 381-388, the pairs being complementary by being aligned on opposing sides of the hub 380.

The hub 380 of FIG. 15 is a radial connector with complementary holes opposite each other on first and second sides of the hub 380. In some embodiments, each pair of holes on opposite sides of the hub 380 open to the same lumen going from the first side of the hub 380 to the second side of the hub 380. The lumen may be defined by a conductive metal sleeve 395. If an electrical wire opposing a conductor are both inserted into opposite sides of the same lumen of the hub 380, such as conductors 366 and electrical wire 387 being inserted into sleeve 395, then electrical connections can be made between the conductor 366 and the electrical wire 387. In some cases, the conductors will respectively touch the electrical wires within the lumens to establish the electrically connectivity. In some cases, the electrical connectivity is established by a conductor complementary with an electrical wire touching the walls of a lumen, such as conductors 366 and electrical wire 387 physically contacting the walls of the sleeve 395.

In some embodiments, the hub 380 includes windows, such as window 396 within sleeve 395. A weld connection can be made between complementary pairs of the electrical wires and conductors through the windows. For example, a mechanical and electrical connection between conductor 366 and electrical conductor 387 can be made within the sleeve 395 by welding the conductor 366 and electrical conductor 387 together through the window 396. In this way, respective electrical connections can be made between electrical wires 381-388 and conductors 360-367.

FIG. 15 illustrates a gap between the outer surface of the lead end 390 and the outer surface of the main lead body 389. These outer surfaces can be bridged by injecting polymer material or adhesive into the gap to define a continuous round outer surface between the outer surfaces of the lead end 390 and the main lead body 389. The Polymer fill or adhesive can partially or fully encapsulate the hub 380, electrical wires 381-388, and conductors 360-367. The injection of polymer fill or adhesive can insulate the electrical wires 381-388 and conductors 360-367, as well as mechanically connect the lead end 390 and the main lead body 389. In some embodiments a cover can be placed over the gap, with or without polymer fill or other insulating material underneath the cover. For example, a shrink tube can be placed over the gap and heated to shrink down over the gap. A cover can be made from other materials, such as a metal sleeve, underneath which polymer fill or adhesive can be deposited to insulate the electrical wires 381-388 and conductors 360-367.

Figure 16:
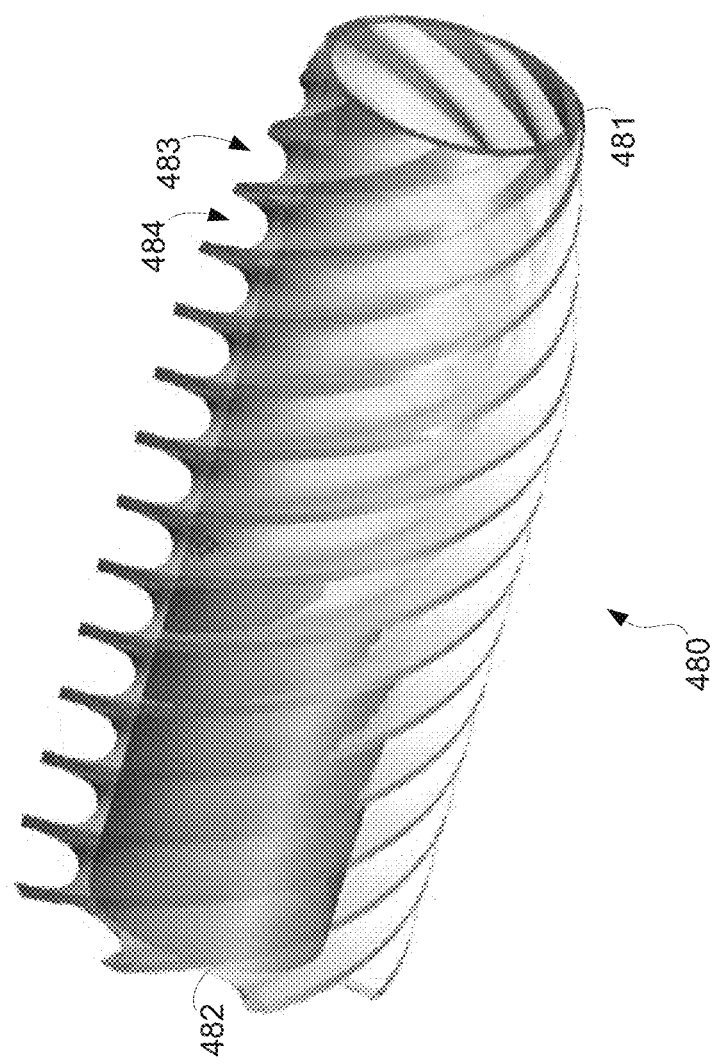
FIG. 16 illustrates a helical hub.

While the hub 380 of FIG. 15 is in the form of a round disc with holes running from one side of the hub 380 to the other side of the hub 380, hubs of various other embodiments may have different configurations. For example, FIG. 16 illustrates a hub 480 having a distal end 481, a proximal end 482, and lumen going from the distal end 481 to the proximal end 482. The hub 480 includes a plurality of channels that spiral around the periphery of the hub 480 from the distal end 481 to the proximal end 482, such as channels 483 and 484. Hub 480 can be used to arrange conductors and electrical wires to align for electrically connecting conductors of a lead end with electrical wires of a main lead body. For example, conductors of a lead end can be placed in the channels of the hub 480 along the proximal end 482 and electrical wires of a main lead body can be placed in the channels of the hub 480 along the distal end 481. The conductors of the lead end and/or the electrical wires of main lead body can be wound around the hub 480 within their respective channels until they meet up along the hub 480. The conductors and the electrical wires can then be welded, crimped, or otherwise mechanically and electrically connected to make electrical connections between conductors of a lead end and the electrical wires of a main lead body. The spiraling channels of the hub 480 provides for arranging the conductors of the lead end or the electrical wires of the main lead body to correspondingly line up with the other of the conductors of the lead end or the electrical wires of the main lead body. Furthermore, the spiraling channels of the hub 480 provides for electrical isolation of the conductors and the electrical wires.

The hub 480 of FIG. 16 can substitute for the hub 380 of FIG. 15, where the hub 480 is placed between the main lead body 389 and the lead end 390. The wires 381-388 of the main lead body 389 can be wound around the hub 480 within the channels, starting at the proximal end 481. Likewise, the conductors 360-367 of the lead end 390 can be wound around the hub 480 within the channels, starting at the distal end 481. The conductors 360-367 and the electrical wires 381-388 can be welded together at the locations in the channels at which they overlap or otherwise meet.

Figure 17:
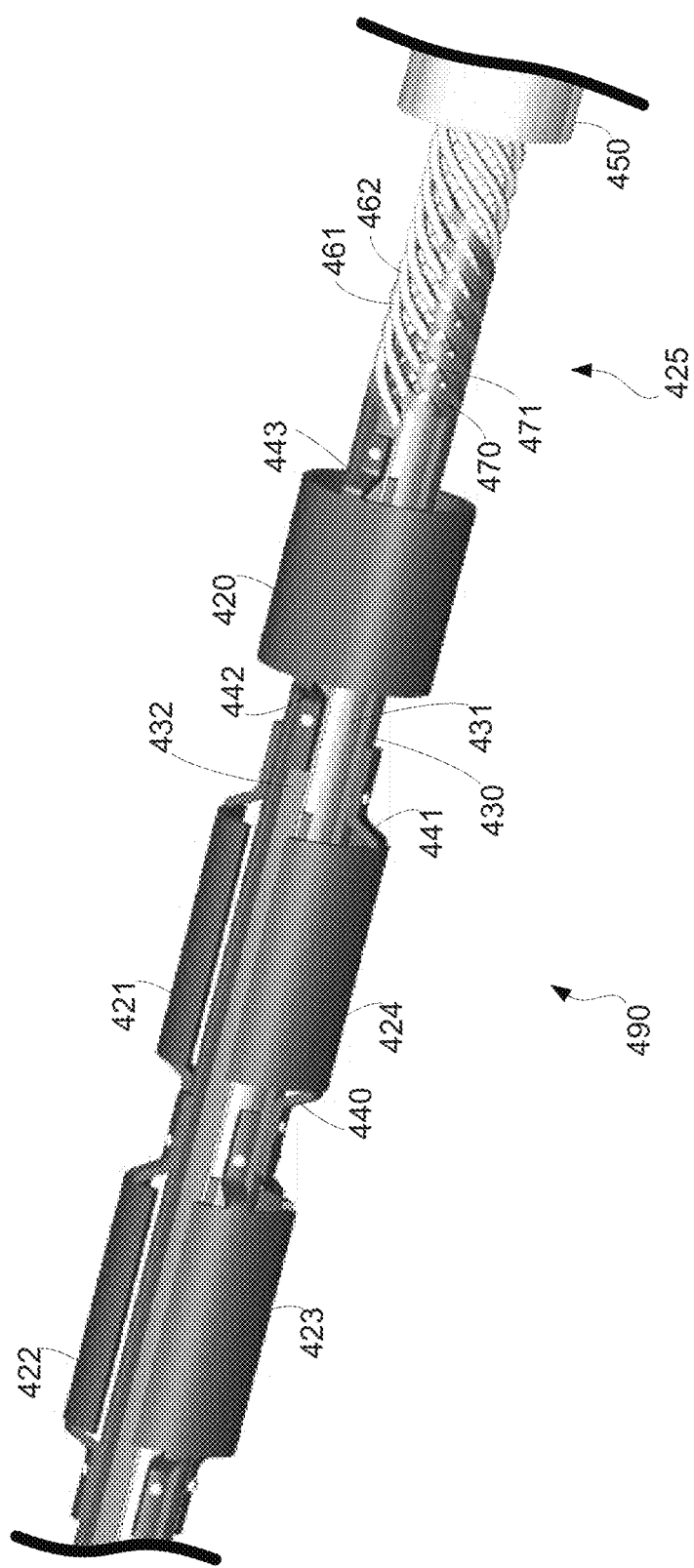
FIG. 17 illustrates connecting a main lead body to a modular lead end.

FIG. 17 illustrates a modular lead embodiment. FIG. 17 shows a lead end 490 built around a spine. The spine is composed of a plurality of spine elements, such as spine elements 430-432. The spine elements 430-432 can be elongated metal elements having straight sections and twisted sections. The spine elements are twisted along the modular connector section 425. Connected to each spine element is at least one electrical element (e.g., contact ring, ring electrode, segmented electrode). For example, contact ring 420 is mechanically and electrically connected to spine element 432 by tabs 442 and 443, the tabs 442 and 443 being conductive. The tabs 442 and 443 can be welded, stamped, crimped, or attached by another technique to the contact ring 420. The tabs 440 and 441 can be welded, bolted, crimped, or attached by another technique to the spine element 430. Segmented electrode 423 is attached to spine element 431. Segmented electrodes 421 and 422 are also connected to respective spine elements obscured in the view of FIG. 17.

The spine elements are arrayed in a circular configuration to form an elongated spine having a circular profile along the length of the spine. The spine elements may be bonded together by polymer, the spine elements joined together by the polymer in an insert molding process. Such an injection molding process may be performed before electrical elements (e.g., segmented electrode 423 and contact ring 420) are mechanically and electrically joined to the spine elements.

Once electrical elements have been loaded into the spine elements, the subassembly can be placed in an injection mold die. And described herein, polymer fill can be injected to partially encapsulate and bind the components of the lead end 490 and define an exterior surface of the lead end between the segmented electrodes 421-424 and ring electrode 420. The lead end 490 would typically have such an injection molding process be performed to fill out the exterior surface of the lead end 490 before the lead end 490 is connected to the main lead body 450. However, for the purpose of clarity in the illustration of FIG. 17, the polymer fill which would be between the segmented electrodes 421-424 and ring electrode 420 defining the exterior surface is not shown in FIG. 17.

The modular connector section 425 of the lead end 490, which comprises the twisted sections of the spine elements, can constitute conductors, such as twisting conductors 470-471, which can individually align with electrical wires of the main lead body 450, such as electrical wires 461-462. As show in FIG. 17, the electrical wires of the main lead body 450 are in a spiraling coil configuration. As such, the spiraling electrical wires of the main lead body 450 can be cut in a line to align with the twisted conductors of the modular connector section 425. When aligned, each of the pairings of aligned twisted conductors and spiraling electrical wires can be welded, crimped, or otherwise mechanically and electrically connected to complete electrical connections between the lead and 490 and the main lead body 450. For example, conductor 470 twists to have its end align in a spiraling configuration with an end of the spiraling electrical wire 461. The conductor 470 and the electrical wire 461 can be crimped, welded, or in some other manner electrically and mechanically connected to one another where they meet and/or overlap. Likewise, electrical conductor 471 twists to align in a spiraling configuration with spiraling electrical wire 462 and the conductor 470 and the electrical wire 461 can be electrically and mechanically connected to one another where they meet and/or overlap.

The gap between the lead end 490 and the main lead body 450 can be completed by any technique described herein for connecting a lead end to a main lead body. For example, the gap between the lead end 490 and the main lead body 450 can be filled in with polymer fill through an injection molding process to form a cylindrical profile and a smooth outer surface between the lead end 490 and the main lead body 450. The polymer fill can electrically insulate the exposed twisted conductors of the modular connector section 425 and the spiraling electrical wires of the main lead body 450.

Figure 18:
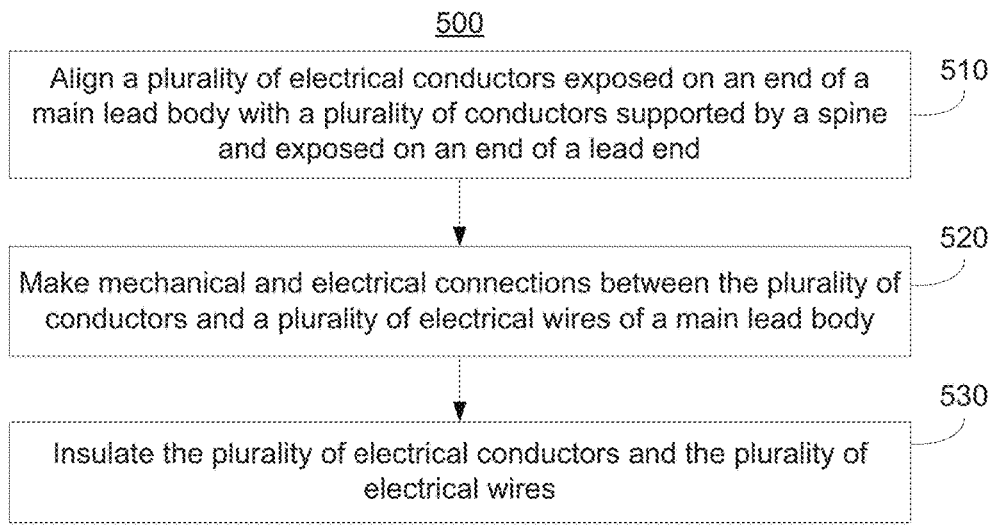
FIG. 18 illustrates a flow chart of a method of making a modular lead end.

FIG. 18 illustrates a flow chart of a method 500 for making a modular lead. The method 500 can correspond to the steps described and illustrated in connection with FIGS. 1-17, for example. The method 500 includes aligning 510 a plurality of electrical wires exposed on an end of a main lead body with a plurality of conductors supported by a spine and exposed on an end of a lead end. The plurality of conductors can be supported in paths of the spine. The lead end may correspond to the proximal lead end 102, distal lead end 103, lead ends 290, 390, and/or 490, or other lead end. The spine may be any spine referenced herein. Alignment may be facilitated by an arrangement of the plurality of conductors of the lead end. In some cases, the plurality of conductors of the lead end are circumferentially arrayed about the spine, as in FIG. 7 (where the conductors of the lead end 290 along the proximal section 225 may correspond to the plurality of conductors of the lead end of the method 500) and/or in FIG. 14 (where the conductors 360-368 of the lead end 390 may correspond to the plurality of conductors of the lead end of the method 500). In some cases, the arrangement of the plurality of conductors of the lead end may have the plurality of conductors being splayed in a circular pattern as illustrated in FIG. 14 (where the conductors 360-368 of the lead end 390 may correspond to the plurality of conductors of the lead end of the method 500) or in a helical arrangement as in FIG. 17 (where the twisted conductors of the modular connector section 425 may correspond to the plurality of conductors of the lead end of the method 500).

Aligning 510 may be facilitated by an arrangement of the plurality of electrical wires. Such an arrangement may comprise the plurality of electrical wires being splayed in a circular arrangement as shown in FIG. 9, for example. Aligning 510 may be facilitated by a hub. For example, the hubs 380 and 480 of FIGS. 15 and 16 may be used to align conductors and electrical wires.

The method 500 further includes making 520 mechanical and electrical connections between the plurality of conductors and a plurality of electrical wires of a main lead body. In some cases, making 520 mechanical and electrical connections between the plurality of electrical wires and the plurality of conductors comprises welding the plurality of electrical wires to the plurality of conductors and/or crimping the plurality of electrical wires to the plurality of conductors. The conductors and electrical wires may be aligned to facilitate making 520 the connections. For example, the conductors and electrical wires may be in respective arrangements that align pairs of conductors and electrical wires. In some embodiments, connections between conductors and electrical wires may be facilitated by a hub. For example, the hub may be used to align individual conductors and electrical wires by inserting electrical wires and conductors into complementary holes on opposite sides of the hub.

The method 500 further includes insulating 530 the plurality of electrical wires and the plurality of conductors. Insulating 530 can include joining the lead end to the main lead body and forming an exterior of a lead between the main lead body and lead end, the exterior of the lead having a cylindrical profile. In some cases, insulating the plurality of electrical wires and the plurality of conductors comprises depositing polymer material around the mechanical connections between the plurality of electrical wires and the plurality of conductors to form a round lead exterior over the mechanical connections. Polymer material may be deposited by an injection molding process.

The method 500 can be preceded by forming the lead end by spacing the plurality of exposed electrical elements along the spine, making electrical connections between the plurality of exposed electrical elements and the plurality of conductors, and forming the exterior surface by adding polymer between the plurality of exposed electrical elements, or other technique for forming a modular lead end. It is noted that the techniques, features, and options described in connection with the embodiments of FIGS. 1-17 can be used in the method 500. Likewise, the process of the method 500 can be used in making a modular lead corresponding to any of the embodiments of FIG. 1-17.

Figure 19:
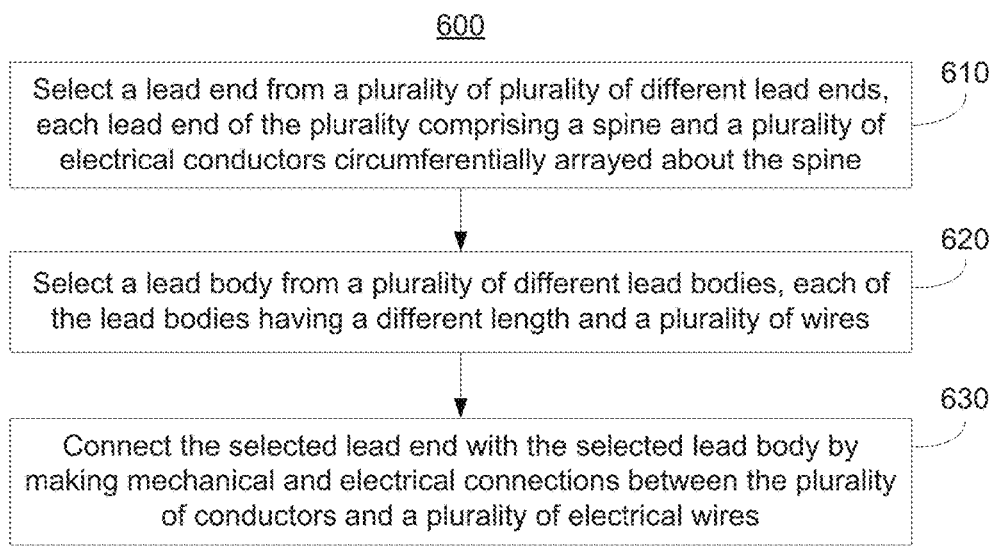
FIG. 19 illustrates a flow chart of a method of making a modular lead end.

FIG. 19 illustrates a flow chart of a method 600 for making a modular lead. The method 600 is particularly applicable in situations where a variety of different types of lead ends (distal and/or proximal) and a variety of different types of main lead bodies have already been constructed, and one or more modular leads is to be made by joining the lead ends and main lead bodies.

The method 600 includes selecting 610 a lead end from a plurality of different lead ends, each lead end of the plurality comprising a spine and a plurality of conductors circumferentially arrayed about the spine. The lead ends may each have an outer surface comprising a plurality of electrical elements and polymer material, the plurality of electrical elements arrayed on the spine and electrically connected with the plurality of conductors, the plurality of electrical elements exposed on the outer surface in a pattern. The lead ends may be different by having different patterns of the plurality of electrical elements on the outer surface. For example, one type of lead end may have only ring electrodes and another type of lead end may have ring electrodes and segmented electrodes. In some cases the different lead ends will have similar types of electrical elements but will have a different number of them, such as four ring electrodes in one type of lead end and eight ring electrodes in another type of lead end.

Selecting 610 each lead end may be done on the basis of which type of lead end is needed for a particular application. For example, if a lead having many contacts is needed, then a lead end having an appropriate number of contacts may be selected 610. If the lead ends have different dimensions and a particular application requires a smaller lead end, then a smaller lead end may be selected 610 over larger lead ends.

The method further includes selecting 620 a lead body from a plurality of different lead bodies, each of the different lead bodies having a different length and a plurality of electrical wires. It is noted that the method 600 of FIG. 19 can be changed such that some or all of the lead bodies have the same length but are different in another aspect, such as the number of conductors that run through the lead body or the outer diameter of the lead body. A lead body may be selected 620 on the basis of the application for which the modular lead is intended. For example, a longer main lead body may be selected 620 for some applications requiring greater distance between the implant location of the IMD and the lead distal end.

The method 600 further includes connecting 630 the selected lead end with the selected lead body by making mechanical and electrical connections between the plurality of electrical wires and the plurality of conductors. Making the mechanical and electrical connections between the plurality of electrical wires and the plurality of conductors may be done in the same manner of making 520 mechanical and electrical connections of the method 500 of FIG. 18, including aligning and welding and/or crimping the electrical wires and the connectors. The electrical wires and/or conductors may be formed into an arrangement for quickly aligning individual pairs of electrical wires and conductors. Alignment of electrical wires and conductors may be done in the manner of FIGS. 9, 15, and 17, for example. It is noted that the techniques, features, and options described in connection with the embodiments of FIGS. 1-17 can be used in the method 600. Likewise, the process of the method 600 can be used in making a modular lead corresponding to any of the embodiments of FIG. 1-17. It is also noted that the methods 500 and 600 may be used together for making a modular lead.

Although various embodiments described herein concern the use of injection molding, various embodiments may additionally or alternatively use a reflow process. Polymer cuffs can be loaded onto a spine. The polymer cuffs can correspond to the polymer sections 260-272 of FIG. 7, for example. The polymer cuffs can be loaded onto the spine alternating with electrical elements (e.g., ring electrodes) or could be slit and put on the spine after all of the electrical elements have been loaded onto the spine. A shrink tube can then be placed over the polymer cuffs and the shrink tube heated (e.g., by a heat element or blowing hot air over the shrink tube). The shrink tube can shrink in response to the heat, applying pressure to the polymer cuffs while also transferring heat to the polymer cuffs. The polymer material can then flow around the spine. It is noted that this technique may be used without polymer cuffs following an injection molding process (e.g., to the embodiment of FIG. 7) to smooth any edges.

Although the use of different spines and techniques for the construction of various lead ends is provided in multiple examples herein, these components, features, and techniques of the various examples are not limited to the embodiments provided. For example, some of the components of one example can be mixed with some of the components of another example. Some of the components and techniques described in connection with the assembly of a distal lead end can be used for the assembly of a proximal lead end, while some of the components and techniques described in connection with the assembly of a proximal lead end can be used for the assembly of a distal lead end. It is also noted that the number of electrical elements illustrated in the various Figures is not intended to limit the number of electrical elements on a lead end constructed around a spine. One, two, three, four, eight, ten, sixteen, or any other number of electrical elements can be placed on a lead end using the techniques discussed herein.

Although the examples presented herein generally describe a single lead to conduct electrical energy between an IMD and tissue, multiple leads may be used in accordance with the devices and methods of the present disclosure. In some cases, multiple leads are used in parallel, where the multiple leads respectively connect to one IMD. In some cases, multiple leads are connected serially, where at least one of the leads serves as a lead extension. It is noted that the devices and methods presented herein are applicable to lead extensions and other leads that bridge electrical connections. For example, the construction of a proximal end and/or a distal end of a lead extension could be done in accordance with the present disclosure (e.g., having modularity), where the proximal end plugs into an IMD and the distal end mechanically and electrically connects with another lead. The distal and/or proximal ends of the lead mechanically and electrically connected with the lead extension can additionally or alternatively be constructed in accordance with the present disclosure (e.g., having modularity).

The various techniques, features, and components discussed herein in various embodiments are applicable to various other embodiments in different configurations and combinations, as the present disclosure makes use of examples to illustrate options which are not limited to the specific embodiments presented. The present disclosure is presented using examples to illustrate and describe various aspects of a lead end having a spine. Each example and set of examples are presented herein to exemplify various features and options. As such, each example embodiment should be understood to be selectively combinable and modifiable in view of the other embodiments presented herein. The specific examples and options are therefore described in a broadening sense and not in a limiting sense.

We claim:

1. A modular lead end comprising:
   a spine formed from a polymer material and extending over a length from a proximal end thereof to a distal end thereof, the spine comprising a plurality paths extending lengthwise, and a plurality of projection sets spaced apart from one another along the length of the spine, each projection set including a plurality of outward extending projections spaced apart from one another around a periphery of the spine, and each path being formed between adjacent projections within each projection set;
   a plurality of electrical elements, each electrical element extending over, and being supported by a corresponding projection set of the spine so that an inner surface of each electrical element faces the corresponding projection set, the inner surface of each electrical element being terminated by an edge that defines an end of the corresponding electrical element, each electrical element including an inward projection engaged with one of the plurality of projections of the corresponding projection set of the spine;
   a plurality of conductors, each conductor extending within a respective path of the plurality of paths of the spine, and each conductor including a feature that projects outward from the corresponding path and abuts the edge of a corresponding electrical element; and
   a plurality of electrical connections, each connection comprising a weld between the feature of each conductor and the corresponding electrical element where the feature abuts the edge of the electrical element; and
   wherein a degree to which the feature of each conductor projects outward prevents movement of the feature past the edge and along the inner surface of the corresponding electrical element.

2. The modular lead end of claim 1, wherein each inward projection engaged with one of the plurality of projections of the corresponding projection set of the spine is located at an inner periphery of each electrical element, the inward projection engaged with the corresponding projection set to prevent movement in one or more directions and such that a portion of the corresponding projection set is uncovered by the electrical element.

3. The modular lead end of claim 2, wherein:
the plurality of electrical elements comprise a plurality of electrodes;
the spine further comprises a proximal section extending between the plurality of projection sets and the proximal end of the spine, the proximal section having a plurality of longitudinal channels arrayed around a circumference of the spine, the channels being aligned with the paths; and
each conductor extends within a corresponding channel of the plurality of longitudinal channels of the spine proximal section so that a proximal end of each conductor is aligned with the proximal end of the spine.

4. The modular lead end of claim 3, further comprising:
a plurality of polymer sections extending around the spine and being spaced from one another along the length of the spine; and
wherein each electrode is located between each adjacent pair of polymer sections, being in contact therewith proximally and distally; and
the proximal section of the spine extends between the plurality of polymer sections and the proximal end of the spine.

5. The modular lead end of claim 1, wherein the end of each electrical element is circular, and the feature of each conductor comprises a circular end matching up with the circular end of the corresponding electrical element.

6. The modular lead end of claim 5, wherein:
the plurality of electrical elements comprise a plurality of electrodes;
the spine further comprises a proximal section extending between the plurality of projection sets and the proximal end of the spine, the proximal section having a plurality of longitudinal channels arrayed around a circumference of the spine, the channels being aligned with the paths; and
each conductor extends within a corresponding channel of the plurality of longitudinal channels of the spine proximal section so that a proximal end of each conductor is aligned with the proximal end of the spine.

7. An implantable lead comprising:
a main lead body including a plurality of electrical wires;
a modular lead end comprising:
a spine formed from a polymer material and extending over a length from a proximal end thereof to a distal end thereof, the spine comprising a plurality paths extending lengthwise, and a plurality of projection sets spaced apart from one another along the length of the spine, each projection set including a plurality of outward extending projections spaced apart from one another around a periphery of the spine, and each path being formed between adjacent projections within each projection set;
a plurality of electrodes, each electrode extending over, and being supported by a corresponding projection set of the spine so that an inner surface of each electrode faces the corresponding projection set, the inner surface of each electrode being terminated by an edge that defines an end of the corresponding electrode, each electrode including an inward projection engaged with one of the plurality of projections of the corresponding projection set of the spine;
a plurality of conductors, each conductor extending within a respective path of the plurality of paths of the spine, each conductor including a feature that projects outward from the corresponding path and abuts the edge of a corresponding electrode, each conductor having a proximal end aligned with the proximal end of the spine, and each conductor, in proximity to the proximal end thereof, being overlapped by a corresponding wire of the plurality of electrical wires of the main lead body; and
a plurality of electrical connections, each connection comprising a weld between the feature of each conductor and the corresponding electrode where the feature abuts the edge of the electrode; and
a plurality of joints, each joint formed between one of the plurality of electrical wires and a corresponding conductor where the wire overlaps the conductor; and
wherein a degree to which the feature of each conductor projects outward prevents movement of the feature past the edge and along the inner surface of the corresponding electrode.

8. The lead of claim 7, wherein each inward projection engaged with one of the plurality of projections of the corresponding projection set of the spine is located at an inner periphery of each electrical element, the inward projection engaged with the corresponding projection set to prevent movement in one or more directions and such that a portion of the corresponding projection set is uncovered by the electrical element.

9. The lead of claim 8, wherein the end of each electrode of the modular lead end is circular, and the feature of each conductor of the modular lead end comprises a circular end matching up with the circular end of the corresponding electrode.

10. The lead of claim 9, wherein:
the spine of the modular lead end further comprises a proximal section extending between the plurality of projection sets and the proximal end of the spine, the proximal section having a plurality of longitudinal channels arrayed around a circumference of the spine, the channels being aligned with the paths; and
each conductor of the modular lead end extends within a corresponding channel of the plurality of longitudinal channels of the spine proximal section.

11. The lead of claim 8, wherein:
the spine of the modular lead end further comprises a proximal section extending between the plurality of projection sets and the proximal end of the spine, the proximal section having a plurality of longitudinal channels arrayed around a circumference of the spine, the channels being aligned with the paths; and
each conductor of the modular lead end extends within a corresponding channel of the plurality of longitudinal channels of the spine proximal section.

12. The lead of claim 7, wherein:
the spine of the modular lead end further comprises a proximal section extending between the plurality of projection sets and the proximal end of the spine, the proximal section having a plurality of longitudinal channels arrayed around a circumference of the spine, the channels being aligned with the paths; and
each conductor of the modular lead end extends within a corresponding channel of the plurality of longitudinal channels of the spine proximal section.

* * * * *